US012790297B2

(12) United States Patent
Wu et al.

(10) Patent No.: US 12,790,297 B2
(45) Date of Patent: Nov. 10, 2026

(54) PROCESSES FOR THE PREPARATION OF (S)-2-(4-CHLORO-2-METHOXYPHENYL)-2-((3-METHOXY-5-(METHYLSULFONYL)-PHENYL)AMINO)-1-(1H-INDOL-3-YL)-ETHENONE DERIVATIVES

(71) Applicant: KATHOLIEKE UNIVERSITEIT LEUVEN, Leuven (BE)

(72) Inventors: Kai Wu, Shanghai (CN); Rik Oost, Eindhoven (NL); Bertrand Schweitzer-Chaput, Antwerp (BE); Magnus Carl Arne Eriksson, Ravels (BE); Erwin Coesemans, Nijlen (BE)

(73) Assignee: Katholieke Universiteit Leuven, Leuven (BE)

( * ) Notice: Subject to any disclaimer, the term of this patent is extended or adjusted under 35 U.S.C. 154(b) by 376 days.

(21) Appl. No.: 18/571,817

(22) PCT Filed: Jun. 28, 2022

(86) PCT No.: PCT/CN2022/101942
§ 371 (c)(1),
(2) Date: Dec. 19, 2023

(87) PCT Pub. No.: WO2023/274237
PCT Pub. Date: Jan. 5, 2023

(65) Prior Publication Data

US 2024/0308959 A1 Sep. 19, 2024

(30) Foreign Application Priority Data

Jun. 29, 2021 (WO) ................ PCT/CN2021/103244
May 6, 2022 (WO) ................ PCT/CN2022/091064

(51) Int. Cl.
*C07D 209/12* (2006.01)
*C07C 51/60* (2006.01)

(52) U.S. Cl.
CPC ............ *C07D 209/12* (2013.01); *C07C 51/60* (2013.01)

(58) Field of Classification Search
CPC .............................. C07C 51/60; C07D 209/12
See application file for complete search history.

(56) References Cited

FOREIGN PATENT DOCUMENTS

WO WO 2016/180696 11/2016

OTHER PUBLICATIONS

PCT/CN2021/103244, International Search Report, dated Jan. 24, 2022.
PCT/CN2022/101942, International Search Report, dated Dec. 5, 2022.

*Primary Examiner* — Sarah Pihonak
(74) *Attorney, Agent, or Firm* — ICE MILLER LLP

(57) ABSTRACT

The present invention relates to novel chiral synthesis of mono- or di-substituted indole compounds of formula (I)

(I)

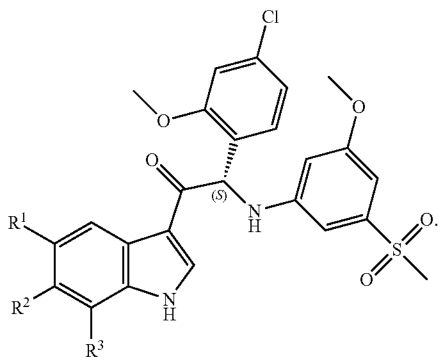

wherein:
$R^1$ is H, $R^2$ is F and $R^3$ is H or $CH_3$,
$R^1$ is H, $CH_3$ or F, $R^2$ is $OCH_3$ and $R^3$ is H and
$R^1$ is H, $R^2$ is $OCH_3$ and $R^3$ is $CH_3$,
$R^1$ is $CH_3$, $R^2$ is F and $R^3$ is H,
$R^1$ is $CF_3$ or $OCF_3$, $R^2$ is H and $R^3$ is H,
$R^1$ is $OCF_3$, $R^2$ is $OCH_3$ and $R^3$ is H and
$R^1$ is $OCF_3$, $R^2$ is H and $R^3$ is $CH_3$.

18 Claims, No Drawings

PROCESSES FOR THE PREPARATION OF (S)-2-(4-CHLORO-2-METHOXYPHENYL)-2-((3-METHOXY-5-(METHYLSULFONYL)-PHENYL)AMINO)-1-(1H-INDOL-3-YL)-ETHENONE DERIVATIVES

CROSS REFERENCE TO RELATED APPLICATIONS

This application is the U.S. national stage of PCT Application No. PCT/CN2022/101942, filed on Jun. 28, 2022, which claims priority to PCT Application No. PCT/CN2022/091064 filed on May 6, 2022 and to PCT Application No. PCT/CN2021/103244 filed on Jun. 29, 2021, the entire contents of which are expressly incorporated herein by reference.

FIELD OF THE INVENTION

The present invention relates to novel chiral syntheses of mono- or di-substituted indole compounds.

BACKGROUND OF THE INVENTION

Flaviviruses, which are transmitted by mosquitoes or ticks, cause life-threatening infections in man, such as encephalitis and haemorrhagic fever. Four distinct, but closely related serotypes of the flavivirus dengue (Dengue virus) are known. WO 2016/180696 discloses mono- or di-substituted indole compounds which show high potent activity against all four (4) serotypes of the Dengue virus and methods to synthesize them. The compounds disclosed in WO 2016/180696 are synthesised using non chiral synthesis methods. Therefore, the desired enantiomer needs to be separated by means of specific procedures. Additionally, synthetic processes that are amenable to industrial set ups are also required. Accordingly, there is a need for chiral synthetic methods for mono- or di-substituted indole compounds.

SUMMARY OF THE INVENTION

To at least partially overcome the problems stated above, the present invention provides a process as defined in the appended claims.

One aspect of the invention is the provision of a process for the preparation of a compound of formula (I)

(I)

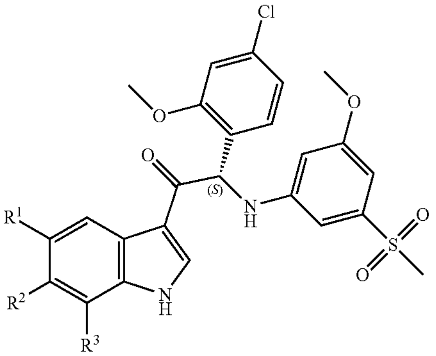

said process comprising the steps of:

a) reacting a compound of formula (II) with 3-methoxy-5-methylsulfonyl-aniline to produce a compound of formula (III); and (II)

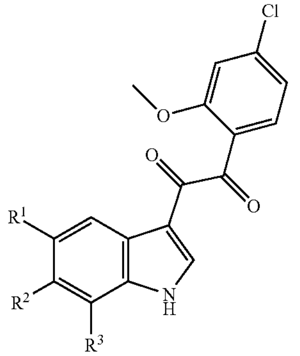

(III)

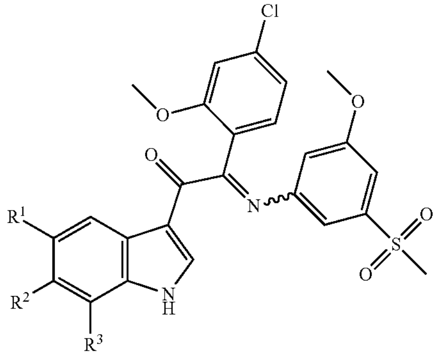

b) hydrogenation of compound of formula (III) to produce compound of formula (I)

wherein:

$R^1$ is H, $R^2$ is F and $R^3$ is H or $CH_3$, $R^1$ is H, $CH_3$ or F, $R^2$ is $OCH_3$ and $R^3$ is H and $R^1$ is H, $R^2$ is $OCH_3$ and $R^3$ is $CH_3$, $R^1$ is $CH_3$, $R^2$ is F and $R^3$ is H, $R^1$ is $CF_3$ or $OCF_3$, $R^2$ is H and $R^3$ is H, $R^1$ is $OCF_3$, $R^2$ is $OCH_3$ and $R^3$ is H and $R^1$ is $OCF_3$, $R^2$ is H and $R^3$ is $CH_3$.

Another aspect of the invention is the provision of a process for the preparation of a compound of formula (I) as described above, said process comprising the steps of:

1) reacting a compound of formula (XXVII) with 3-methoxy-5-methylsulfonyl-aniline in the presence of a phase transfer catalyst to produce compound of formula (XXVIII);

(XXVII)

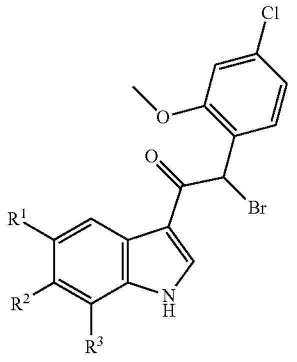

(XXVIII)

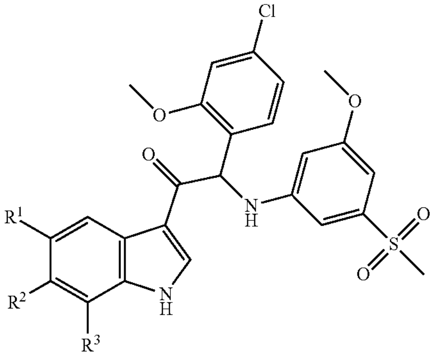

2) chiral separation of compound of formula (XXVIII) to produce compound of formula (I).

DETAILED DESCRIPTION OF THE INVENTION

The disclosure may be more fully appreciated by reference to the following description, including the following glossary of terms and the concluding examples. It is to be appreciated that certain features of the disclosed pharmaceutical formulations and methods which are, for clarity, described herein in the context of separate aspects, may also be provided in combination in a single aspect. Conversely, various features of the disclosed pharmaceutical formulations and methods that are, for brevity, described in the context of a single aspect, may also be provided separately or in any sub-combination. Throughout the description and claims of this specification, the words “comprise” and “contain” and variations of the words, for example “comprising” and “comprises”, mean “including but not limited to”, and are not intended to (and do not) exclude other components.

The recitation of numerical ranges by endpoints includes all integer numbers and, where appropriate, fractions subsumed within that range (e.g., 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g., from 1.0 to 5.0 includes both 1.0 and 5.0). Any numerical range recited herein is intended to include all sub-ranges subsumed therein. All references cited in the present specification are hereby incorporated by reference in their entirety. In particular, the teachings of all references herein specifically referred to are incorporated by reference.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to “one embodiment” or “an embodiment” means that a particular feature, structure, or characteristic described in connection with the embodiment is included in at least one embodiment of the present invention. Thus, appearances of the phrases “in one embodiment” or “in an embodiment” in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art.

The term “chiral synthesis” or “asymmetric synthesis” as used herein refers to a reaction sequence in which one or more new elements of chirality (for instance, a carbon atom becoming a chiral atom) are formed in a substrate molecule and which produces a specific enantiomer or diastereomer.

Pure stereoisomeric forms of the compounds and intermediates as mentioned herein are defined as isomers substantially free of other enantiomeric or diastereomeric forms of the same basic molecular structure of said compounds or intermediates. In particular, the term “stereoisomerically pure” concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms “enantiomerically pure” and “diastereomerically pure” should be understood in a similar way, but then having regard to the enantiomeric excess, respectively the diastereomeric excess of the mixture in question.

The present invention encompasses processes for the preparation of compounds of formula (I). In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in “Protective Groups in Organic Chemistry”, John Wiley and Sons, 1999. Protected forms of the inventive compounds are included within the scope of the present invention. It will also be clear to the skilled person that compounds of the invention in which one or more functional groups have been protected with suitable functional groups can find use as intermediates in the production and/or synthesis of the compounds of the invention, and as such form a further aspect of the invention.

One aspect of the invention is the provision of a process for the preparation of a compound of formula (I)

(I)

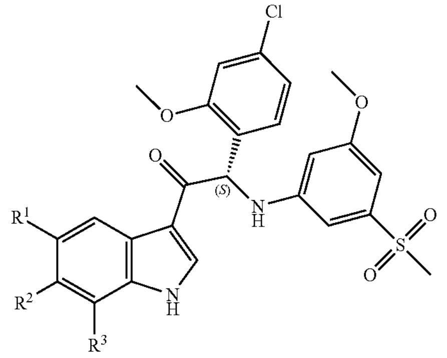

said process comprising the steps of:

a) reacting a compound of formula (II) with 3-methoxy-5-methylsulfonyl-aniline to produce a compound of formula (III); and (II)

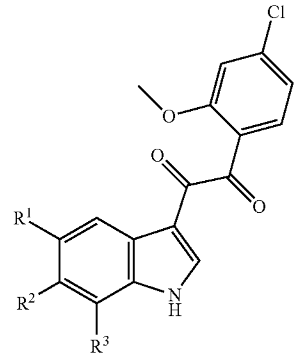

(III)

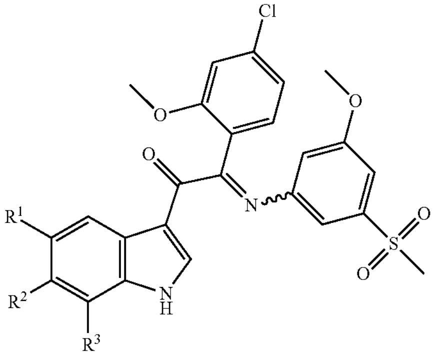

b) hydrogenation of compound of formula (III) to produce compound of formula (I);

wherein:

$R^1$ is H, $R^2$ is F and $R^3$ is H or $CH_3$,
$R^1$ is H, $CH_3$ or F, $R^2$ is $OCH_3$ and $R^3$ is H and
$R^1$ is H, $R^2$ is $OCH_3$ and $R^3$ is $CH_3$,
$R^1$ is $CH_3$, $R^2$ is F and $R^3$ is H,
$R^1$ is $CF_3$ or $OCF_3$, $R^2$ is H and $R^3$ is H,
$R^1$ is $OCF_3$, $R^2$ is $OCH_3$ and $R^3$ is H and
$R^1$ is $OCF_3$, $R^2$ is H and $R^3$ is $CH_3$.

It is to be understood that the wavy line ( ) in the compounds of formula (III) above is meant to indicate that the absolute stereochemistry of the double bond in the compound of formula (III) is an unknown E/Z ratio.

In some embodiments, the step of reacting a compound of formula (II) with 3-methoxy-5-methylsulfonyl-aniline to produce a compound of formula (III) can be performed in the presence of at least one reagent selected from p-TsOH, MSA, TFA, dichloroacetic acid (DCA), saccharin, $Ca(OTf)_2$, $ZnBr_2$ $Zn(OTf)_2$, $TiCl_4$, $Ti(i\text{-}PrO)_4$, $Ti(EtO)_4$, $FeCl_3$, CuBr, $ZnCl_2$, TfOH and $Ba(OTf)_2$.

In some embodiments, the step of hydrogenating the compound of formula (III) to produce a compound of formula (I) is performed in the presence of a combination of a catalyst and a chiral ligand. The catalyst can be bis(norbornadiene)rhodium(I)tetrafluoro-borate and the chiral ligand can be (S)-1-[(RP)-2-(diphenylphosphino)ferrocenyl]ethyldi-tert-butylphosphine. In some embodiments, the ratio of rhodium to phosphine is from 1:1 to 3:1, preferably from 1:2 to 2:1, more preferably 1:1.

Alternatively, the hydrogenation of the compound of formula (III) to produce a compound of formula (I) is performed in the presence of a combination of the ruthenium catalyst $Ru(COD)(TFA)_2$ (i.e. (1Z,5Z)-cycloocta-1,5-diene; ruthenium($2^+$); 2,2,2-trifluoroacetate) and the chiral ligand (S)-DM-SEGPHOS (i.e. (S)-(−)-5,5'-bis(diphenyl-phosphino)-4,4'-bi-1,3-benzodioxole). The ratio of ruthenium catalyst to ligand is from 1:1 to 3:1, preferably from 1:2 to 2:1, more preferably 1:1.

In some embodiments, the compound of formula (II) as defined hereinabove can be prepared by a method comprising the steps of:

i) converting 2-(4-chloro-2-methoxy-phenyl)acetic acid (IX) into a compound of formula (Xa), wherein X is Cl, F or Br; preferably X is Br;

(IX)

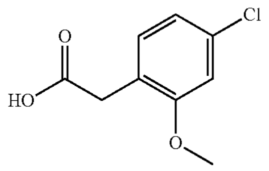

(Xa)

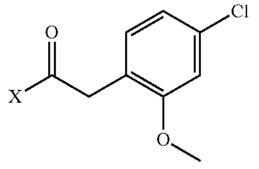

ii) reacting the compound of formula (Xa) with a compound of formula (XI) to produce a compound of formula (XII);

(XI)

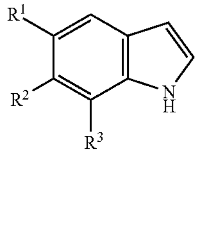

-continued (XII)

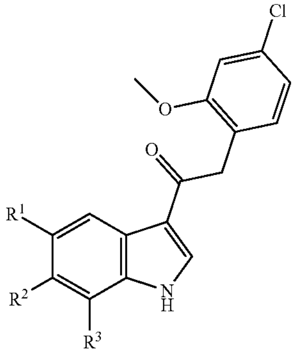

iii) contacting compound of formula (XII) with an oxidizing agent to produce a compound of formula (II);

wherein $R^1$, $R^2$ and $R^3$ are as defined herein.

In some embodiments, the step of converting 2-(4-chloro-2-methoxy-phenyl)acetic acid (IX) into a compound of formula (Xa) can be performed in the presence of at least one reagent selected from $SOCl_2$, $SOBr_2$, oxalyl chloride, $PCl_5$, $PCl_3$, or $PBr_3$.

In some embodiments, the step of reacting compound of formula (Xa) with a compound of formula (XI) to produce a compound of formula (XII) can be performed in the presence of at least one reagent selected from $Et_2AlCl$ or $AlCl_3$. Preferably, the amount of reagent used is ranging from 0.5 to 3 equivalents; more preferably from 1 to 2 equivalents, most probably from 1.2 to 1.5 equivalents. This step can be carried out in a suitable solvent such as toluene, $CH_2Cl_2$, or 1,2-dichloroethane.

In some embodiments, the step of contacting compound of formula (XII) with an oxidizing agent to produce a compound of formula (II) can be performed in the presence of at least one oxidizing agent preferably selected from $I_2$/dimethyl sulfoxide (DMSO), N-iodosuccinimide (NIS)/DMSO, $SeO_2$, o-iodobenzoic acid, potassium permanganate supported on manganese dioxide, selenium dioxide, bismuth/picolinic acid, $Co(OAc)_2$/TEMPO, or $Co(OAc)_2$/NaClO. In some embodiments, $I_2$/DMSO is used in an amount of from 0.5 to 2.0 equivalents. In some embodiments, NIS/DMSO is used in an amount of from 5 to 28 equivalents. In some embodiments, $SeO_2$ is used in an amount of from 1 to 3 equivalents.

In some embodiments, the compound of formula (II) as defined above can be prepared by a method comprising the steps of i) reacting a compound of formula (XI) with oxalyl chloride to produce a compound of formula (XIII);

(XI)

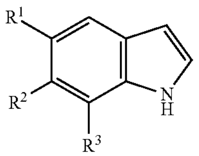

-continued (XIII)

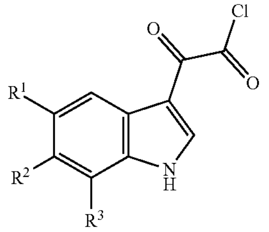

ii) contacting compound of formula (XIII) with a compound selected from the group comprising: (4-chloro-2-methoxyphenyl)magnesium bromide, (4-chloro-2-methoxyphenyl)magnesium chloride, (4-chloro-2-methoxyphenyl)magnesium iodide, (4-chloro-2-methoxyphenyl)Zinc bromide, (4-chloro-2-methoxyphenyl)Zinc chloride and (4-chloro-2-methoxyphenyl)Zinc iodide, to afford a compound of formula (II);

wherein $R^1$, $R^2$ and $R^3$ are as defined herein.

In some embodiments, the compound of formula (II) as defined above is prepared by a method comprising the steps of ia) introducing a protecting group in the compound of formula (XI) to produce a compound of formula (XIa), wherein PG is preferably selected from the group comprising benzyl, p-nitrobenzyl, p-methoxybenzyl, benzhydryl, and allyl;

(XI)

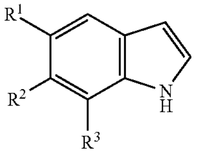

(XIa)

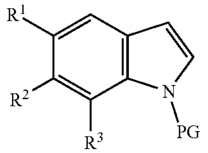

ib) reacting compound of formula (XIa) with oxalyl chloride to produce a compound of formula (XIIIa);

(XIIIa)

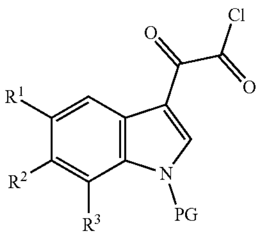

iia) contacting compound of formula (XIIIa) with 4-chloro-2-methoxyphenyl)magnesium halide to afford a compound of formula (IIa); preferably the reaction is performed in the presence of a ligand and/or a catalytic Cu(I) salt;

(IIa)

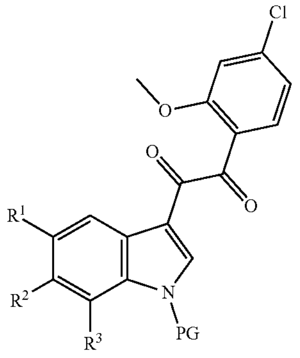

iib) removing protecting group PG from the compound of formula (IIa) to afford compound of formula (II);

wherein $R^1$, $R^2$ and $R^3$ are as defined herein.

The ligand can be selected from the group comprising 2-(dimethylamino)ethyl ether, N,N,N'-pentamethyldiethylenetriamine, N"-pentamethyldiethylenetriamine, N"-pentamethyldiethylenetriamine, and tris2-(dimethylamino)ethylamine. The ligand may be used in an amount ranging from 1 to 3 equivalents; preferably from 1.1 to 3.0 equivalents; preferably from 1.1 to 2.9 equivalents; preferably from 1.2 to 2.8 equivalents.

Non-limiting examples of suitable Cu(I) salts include: CuCl, CuBr, CuI, CuCN or any combination thereof. The Cu(I) salt may be used in an amount ranging from 0.05 to 1.0 equivalents; preferably from 0.6 to 1.0 equivalents; preferably from 0.5 to 0.9 equivalents; preferably from 0.7 to 0.8 equivalents.

In some embodiments, the compound of formula (XIIIa) is contacted with 4-chloro-2-methoxyphenyl)magnesium bromide.

In some embodiments, the benzyl protecting group is removed using at least one oxidizing agent. Non-limiting examples of suitable oxidizing agents include: CrO3/acetic acid at ambient temperature, ozone, N-bromosuccinimide (NBS), and N-iodosuccinimide (NIS). In some embodiments, the p-methoxybenzyl protecting group is removed using an oxidizing agent or strong acidic conditions. Non-limiting examples of suitable oxidizing agents include: CrO3/acetic acid, for example at ambient temperature, ozone, N-bromo-succinimide (NBS), N-iodosuccinimide (NIS), ceric ammonium nitrate (CAN) and dichlorodicyanobenzoquinone (DDQ). In some embodiments, the benzhydryl protecting group is removed by contacting the compound with a 10% triflic acid solution in TFA at 0° C. or with 20% aq NaOH in methanol 75 C. In some embodiments, the allyl protecting group is removed by contacting the compound with $BBr_3$, tert-butyllithium, or $SmI_2/H_2O$/i-$PrNH_2$.

In some embodiments, the compound of formula (II) as defined above can be prepared by a method comprising the steps of:

i) reacting a compound of formula (XI) with oxalyl chloride or oxalyl bromide to produce a compound of formula (XIII);

(XI)

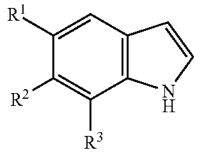

(XIII)

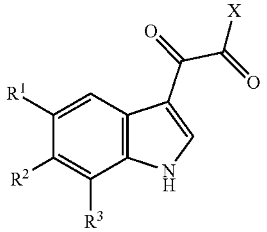

(X=Cl, Br)

ia') contacting compound of formula (XIII) with a compound selected from the group comprising morpholine, N,O-dimethylhydroxylamine, diethyl amine, pyrrolidine, MeNHBoc, $Boc_2NH$, and PhNHBoc, to afford a compound of formula (XIIIa), wherein $R^4$ is selected from the group comprising morpholinyl, N,O-dimethylhydroxylaminyl, diethyl aminyl, pyrrolidinyl, MeNBoc, $Boc_2N$, and PhNBoc; preferably $R^4$ is morpholinyl; and (XIIIa)

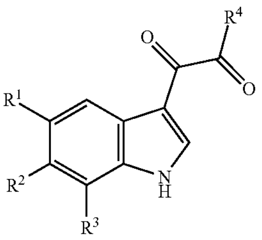

ib') contacting compound of formula (XIIIa) with (4-chloro-2-methoxyphenyl)magnesium halides, to afford a compound of formula (II);

wherein $R^1$, $R^2$ and $R^3$ are as defined herein.

In some embodiments, the step of reacting a compound of formula (XI) or formula (XIa) with oxalyl chloride or oxalyl bromide is performed in the presence of methyl tert-butyl ether (MTBE), THF, MeTHF, or diethyl ether.

In some embodiments, the step of contacting compound of formula (XIIIa) with 4-chloro-2-methoxyphenyl)magnesium halide is performed in the presence of a reagent selected from the group comprising lithium bis(trimethylsilyl)amide (LiHMDS), NaHMDS, KHMDS, LDA, BuLi, MeLi, EtMgBr, tBuMgCl, and iPrMgCl.

In some embodiments, the compound of formula (II) as defined hereinabove is prepared by a method comprising the steps of:

i) reacting a compound of formula (XI) with oxalyl chloride or oxalyl bromide to produce a compound of formula (XIII);

(XI)

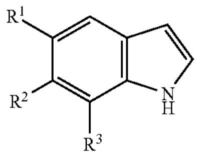

(XIII)

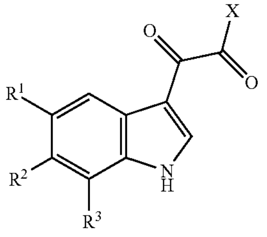

(X═Cl, Br)

ii) reacting a compound of formula (XIII) with 3-chlorophenol to produce a compound of formula (XVI);

(XVI)

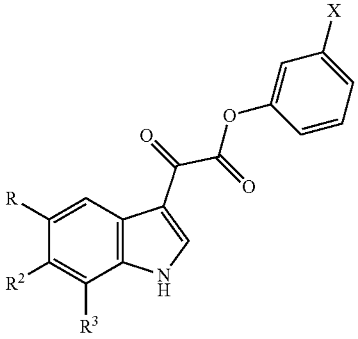

iii) submitting compound of formula (XVI) to acidic conditions to afford compound of formula (XVII);

(XVII)

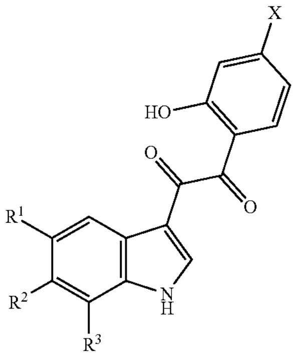

iv) methylation of the compound of formula (XVII) to afford compound of formula (II); wherein $R^1$, $R^2$ and $R^3$ are as defined herein.

In some embodiments, the step of reacting compound of formula (XIII) with 3-chlorophenol to produce a compound of formula (XVI) can be performed in the presence of at least one Lewis base. Non-limiting examples of a suitable Lewis base for this reaction include $Et_3N$, pyridine, N-methylmorpholine, DIPEA, acetonitrile, dimethylacetamide, and dimethyl sulfoxide.

In some embodiments, the compound of formula (II) as defined above can be prepared by a method comprising the steps of i) reacting 4-chloro-2-methoxybenzaldehyde with a compound of formula (XVIII) to afford a compound of formula (XIX), wherein PG is a protecting group, preferably selected from the group comprising benzyl, methyl, acetyl, and tosyl; and

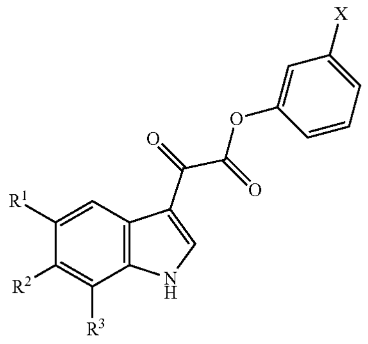

(XVIII)

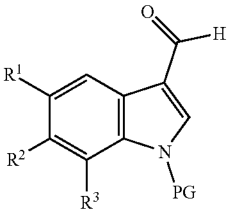

(XIX)

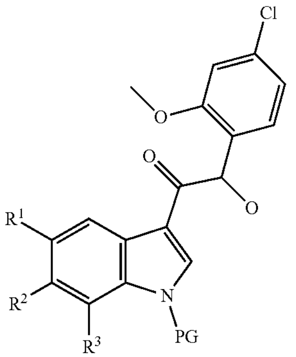

ii) contacting compound of formula (XIX) with an oxidizing agent to produce compound of formula (II);

wherein $R^1$, $R^2$ and $R^3$ are as defined herein.

In some embodiments, the reaction of 4-chloro-2-methoxybenzaldehyde with a compound of formula (XVIII) to afford a compound of formula (XIX) as defined hereinabove is performed in the presence of 6,7-dihydro-2-pentafluorophenyl-5H-pyrrolo[2,1-c]-1,2,4-triazolium tetrafluoroborate (1-20 mol % in 1:1 ratio) and diisopropylethylamine (DIPEA; 1-20 mol % in 1:1 ratio).

Non-limiting examples of suitable oxidizing agents to perform the conversion of a compound of formula (XIX) into a compound of formula (II) include: MeCN in the presence of oxygen and at least one copper salt selected from CuBr, copper(I) thiophene-2-carboxylate (CuTC), and $Cu(OAc)_2$, tetrapropylammonium perruthenate/N-methylmorpholine-N-Oxide (TPAP/NMO), $MnO_2$, 2,2,6,6-Tetramethylpiperidin-1-yl)oxyl, pyridinium chlorochromate (PCC), Dess-Martin Periodinane or (2,2,6,6-tetramethylpiperidin-1-yl)oxidanyl(TEMPO)/oxone and $H_2O_2$.

In some embodiments, the compound of formula (II) as defined hereinabove can be prepared by a method comprising the steps of:

i) reacting 1-(4-chloro-2-methoxy-phenyl)-2,2-dihydroxy-ethanone with a compound of formula (XI) to afford a compound of formula (XX)

(XI)

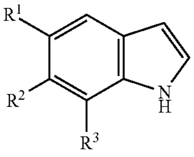

(XX)

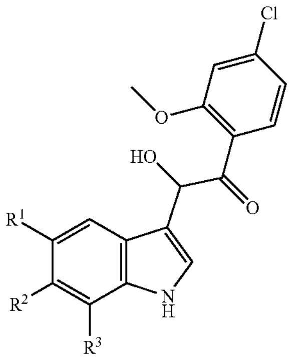

ii) reacting a compound of formula (XX) with an oxidizing agent to afford compound of formula (II);

wherein $R^1$, $R^2$, and $R^3$ are as defined herein.

In some embodiments, the reaction of 1-(4-chloro-2-methoxy-phenyl)-2,2-dihydroxy-ethanone with a compound of formula (XI) to afford a compound of formula (XX) as defined hereinabove is performed in the presence of at least one copper salt such as copper(I) thiophene-2-carboxylate (CuTC), copper(I) bromide (CuBr) and copper(II) acetate (Cu(OAc)2) (each 1-10 mol %).

Non-limiting examples of suitable oxidizing agents to perform the conversion of a compound of formula (XX) into a compound of formula (II) include: MeCN in the presence of oxygen and at least one copper salt selected from CuBr, CuTC and $Cu(OAc)_2$, tetrapropylammonium perruthenate/N-methylmorpholine-N-Oxide (TPAP/NMO), $MnO_2$, 2,2,6,6-Tetramethylpiperidin-1-yl)oxyl or (2,2,6,6-tetramethylpiperidin-1-yl)oxidanyl(TEMPO)/oxone and $H_2O_2$.

In some embodiments, the compound of formula (II) as defined above can be prepared by a method comprising the steps of:

i) reacting a compound of formula (XXV) with a base selected from LiOtBu, LiHMDS, LiOEt, LiOMe and LiOH to produce a compound of formula (XXVI);

(XXV)

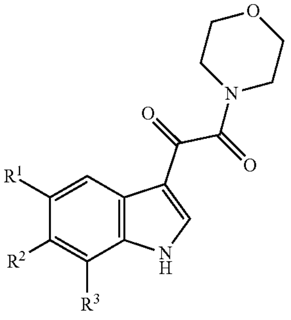

(XXVI)

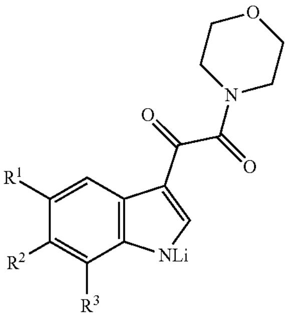

ii) reacting compound of formula (XXVI) with 4-chloro-2-methoxyphenyl magnesium halide or with (4-chloro-2-methoxyphenyl)Lithium to produce compound of formula (II), preferably wherein the halide is Br, Cl or I;

wherein $R^1$, $R^2$ and $R^3$ are as defined herein.

Another aspect of the invention is the provision of a process for the preparation of a compound of formula (I) as defined in the previous aspect, said process comprising the steps of:

1) reacting a compound of formula (XXVII) with 3-methoxy-5-methylsulfonyl-aniline, preferably in the presence of a suitable phase transfer catalyst, to produce compound of formula (XXVIII);

(XXVII)

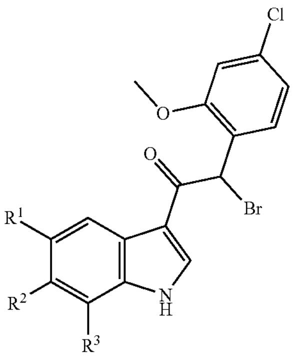

-continued (XXVIII)

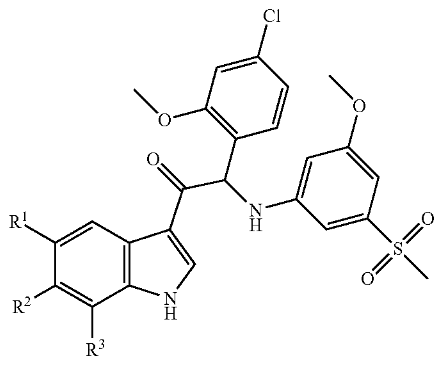

2) chiral separation of compound of formula (XXVIII) to produce compound of formula (I), wherein:

$R^1$ is H, $R^2$ is F and $R^3$ is H or $CH_3$, $R^1$ is H, $CH_3$ or F, $R^2$ is $OCH_3$ and $R^3$ is H and $R^1$ is H, $R^2$ is $OCH_3$ and $R^3$ is $CH_3$, $R^1$ is $CH_3$, $R^2$ is F and $R^3$ is H, $R^1$ is $CF_3$ or $OCF_3$, $R^2$ is H and $R^3$ is H, $R^1$ is $OCF_3$, $R^2$ is $OCH_3$ and $R^3$ is H and $R^1$ is $OCF_3$, $R^2$ is H and $R^3$ is $CH_3$.

As used herein, the term "phase transfer catalyst" preferably refers to a catalyst that facilitates the migration of a reactant from one phase into another phase where reaction occurs. Non-limiting example of suitable phase transfer catalysts to perform the reaction of compound of formula (XXVII) with 3-methoxy-5-methylsulfonyl-aniline include tetrabutylammonium bromide (TBAB), benzyltriethylammonium chloride, methyltricaprylammonium chloride, methyltributylammonium chloride, methyltrioctylammonium chloride, and hexadecyltributylphosphonium bromide.

In some embodiments, the reaction of step (1) is performed in the presence of a buffer solution. Non-limiting examples of suitable buffer solutions include sodium dihydrogen phosphate dihydrate, and dipotassium hydrogen phosphate trihydrate.

In some embodiments, the reaction of step (1) is performed using tetrabutylammonium bromide and a buffer solution of sodium dihydrogen phosphate dihydrate and dipotassium hydrogen phosphate trihydrate.

The step of chiral separation of compound of formula (XXVIII) may be performed by the application of art-known procedures. For instance, enantiomers may be separated from each other by the selective crystallization of their diastereomeric salts with optically active acids or bases. Non-limiting examples thereof include tartaric acid, dibenzoyltartaric acid, ditoluoyltartaric acid, and camphorsulfonic acid. Alternatively, enantiomers may be separated by chromatographic techniques using chiral stationary phases.

In some embodiments, $R^1$ is $OCF_3$, $R^2$ is H and $R^3$ is H.

In some embodiments the compound of formula (I) is:

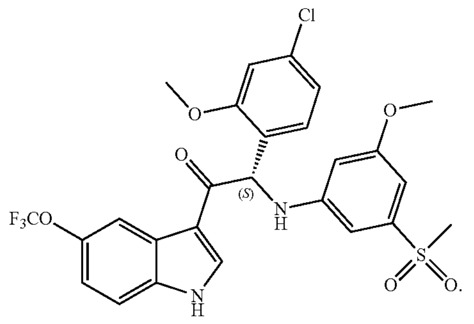

In some preferred embodiments, the process comprises the synthesis of (S)-2-(4-chloro-2-methoxyphenyl)-2-((3-methoxy-5-(methylsulfonyl)phenyl)amino)-1-(5-(trifluoromethoxy)-1H-indol-3-yl)ethenone (D), said process can be performed as outlined in Scheme 1:

Scheme 1

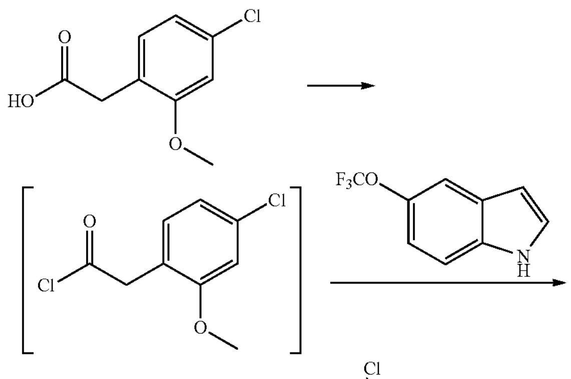

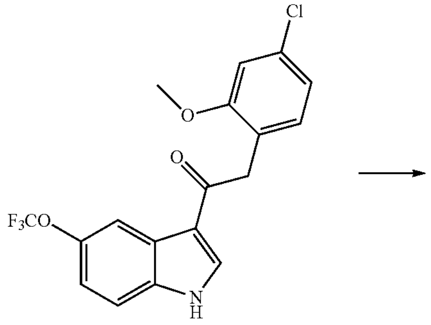

Compound A

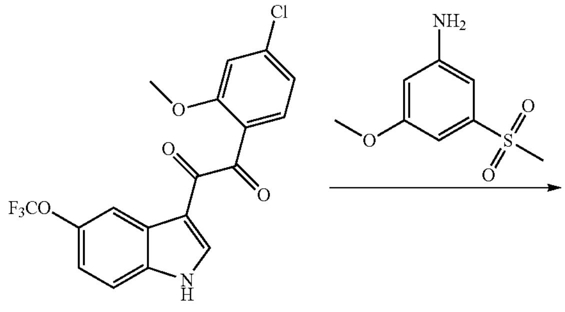

Compound G

-continued

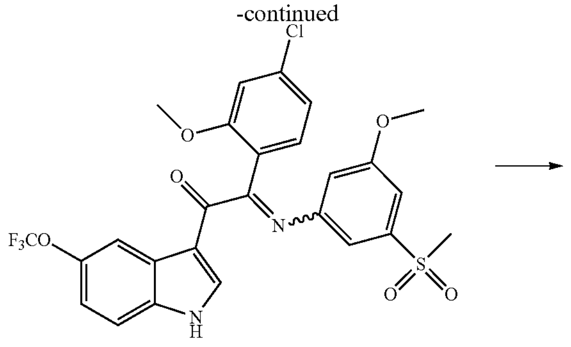

Compound F

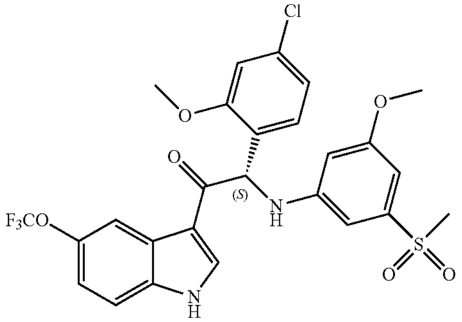

Compound D

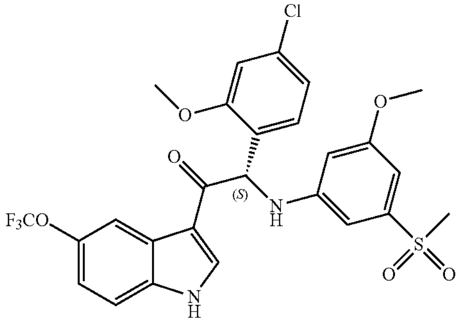

Compound D 2-(4-Chloro-2-methoxyphenyl)acetic acid can be converted to the corresponding 2-(4-chloro-2-methoxyphenyl) acetyl chloride with a chlorination reagent such as for example thionyl chloride. This step can be performed using from 1.0 to 2.0 equivalent of the chlorination reagent, preferably from 1.0 to 1.5 equivalent. This step can be performed at a temperature ranging from 50° C. to 75° C., preferably from 55° C. to 70° C., preferably from 60° C. to 65° C. This step can be performed in the presence of a suitable solvent such as toluene, $CH_2Cl_2$ or 1,2-dichloroethane. The reaction of the 2-(4-chloro-2-methoxyphenyl) acetyl chloride with 5-(trifluoromethoxy)-1H-indole can be performed using a Lewis acid reagent such as for example $Et_2AlCl$, $AlCl_3$ or $TiCl_4$ in a suitable solvent like for example toluene, $CH_2Cl_2$ or 1,2-dichloroethane, thereby obtaining compound A. This step can be performed at a temperature ranging from −20° C. to 5° C., preferably from −15° C. to 0° C., preferably from −10° C. to −5° C. Compound A can then be contacted with an oxidizing agent thereby producing compound G (1-(4-chloro-2-methoxyphenyl)-2-(5-(trifluoromethoxy)-1H-indol-3-yl)ethane-1,2-dione). Non-limiting examples of suitable oxidizing agent can be selected from $I_2$/DMSO ($I_2$ ratio to compound A can be ranging from 0.5 to 2.0 equiv.), NIS/DMSO (DMSO ratio to compound A can be ranging from 5 to 28 equiv.), $SeO_2$, o-iodobenzoic acid, potassium permanganate supported on manganese dioxide, bismuth/picolinic acid, $Co(OAc)_2$/TEMPO [for example using 5 mol % $Co(OAc)_2$ and for example 2 to 3 equiv. TEMPO] or $Co(OAc)_2$/NaOCl [for example using 5 mol % $Co(OAc)_2$ and for example 2 to 3 equiv. NaOCl]. This step can be performed at a temperature ranging from 50° C. to 100° C., preferably from 60° C. to 90° C., preferably from 70° C. to 85° C., preferably 75° C. to 80° C. A non-limiting example of a suitable solvent for this step includes 2-methyl tetrahydrofuran (2-Me-THF) and DMSO. Compound G can then be reacted with 3-methoxy-5-methylsulfonyl-aniline to produce compound F. This step can be performed in the presence of at least one reagent selected from the group comprising $Zn(OTf)_2$, p-TsOH, TFA, dichloroacetic acid (DCA), saccharin, MSA, $Ca(OTf)_2$, $ZnBr_2$, $TiCl_4$, Ti $(i\text{-}PrO)_4$, and $Ti(EtO)_4$. A non-limiting example of a suitable solvent for this step includes 2-methyl tetrahydrofuran (2-Me-THF), toluene or a mixture thereof. Compound F can then be hydrogenated to produce compound D. The hydrogenation step can be performed in the presence of a suitable hydrogenation reagent, such as a combination of bis(norbornadiene)rhodium(I) tetrafluoroborate and (S)-1-[(RP)-2-(diphenylphosphino)ferrocenyl]ethyldi-tert-butylphosphine.

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 2:

Scheme 2

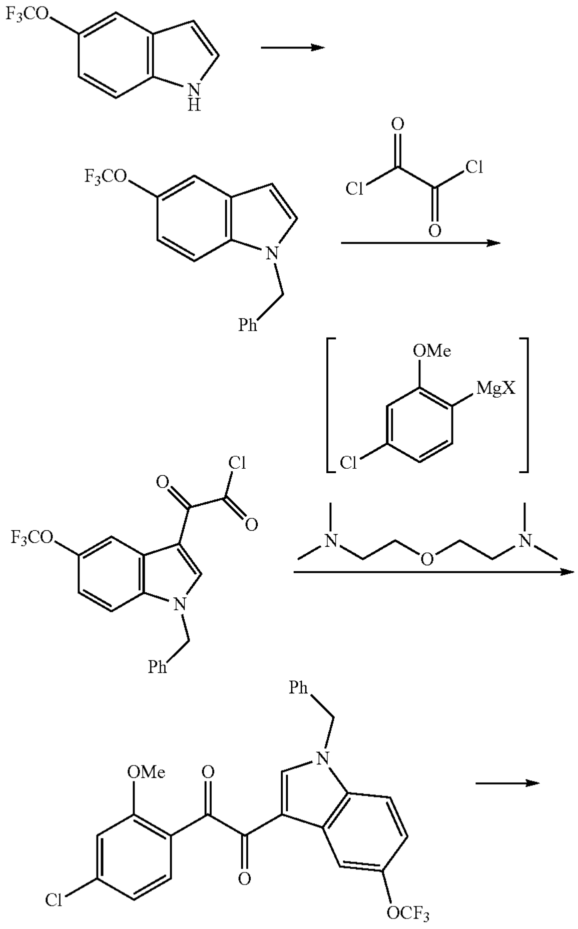

-continued

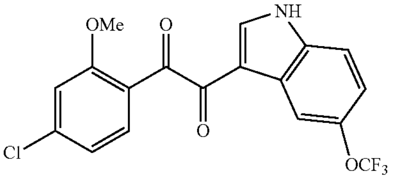

Compound G

The process can comprise converting 5-(trifluoromethoxy)-1H-indole to an N-protected intermediate, such as for example an N-benzyl using a reagent such as for example benzyl bromide, in the presence of a base such as for example potassium-tert-butoxide. The N-protected intermediate can then be reacted with oxalyl chloride to produce 2-[1-benzyl-5-(trifluoromethoxy)indol-3-yl]-2-oxo-acetyl chloride. This step can be performed in the presence of a suitable solvent such as diethyl ether, methyl tert-butyl ether (MTBE), THF, or 2-Me-THF. This step can be performed at a temperature ranging from 0° C. to room temperature. 2-[1-Benzyl-5-(trifluoromethoxy)indol-3-yl]-2-oxo-acetyl chloride can then be reacted with (4-chloro-2-methoxyphenyl)magnesium halide (X can be bromide for example), for example in the presence of bis[2-(N,N-dimethylamino) ethyl] ether, to give the 1-[1-benzyl-5-(trifluoromethoxy) indol-3-yl]-2-(4-chloro-2-methoxy-phenyl)ethane-1,2-dione. The dione can then be hydrogenated to yield intermediate compound G. The hydrogenation and thereby removal of the benzyl protecting group can be performed using $H_2$ in the presence of a suitable catalyst such as palladium on carbon (Pd/C).

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 3:

Scheme 3

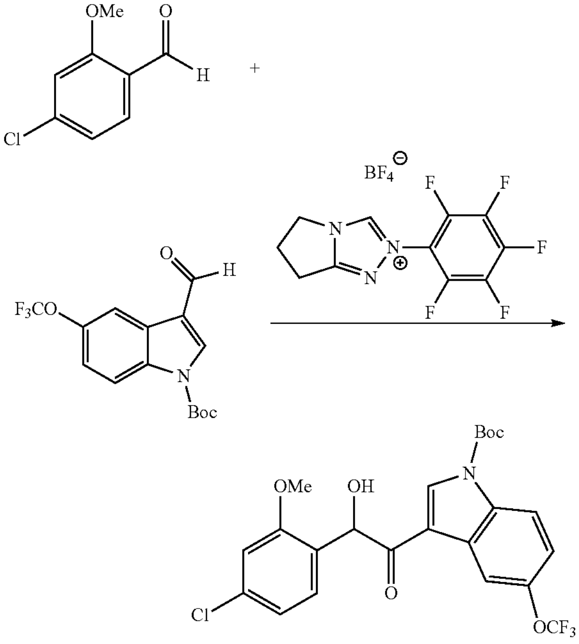

-continued

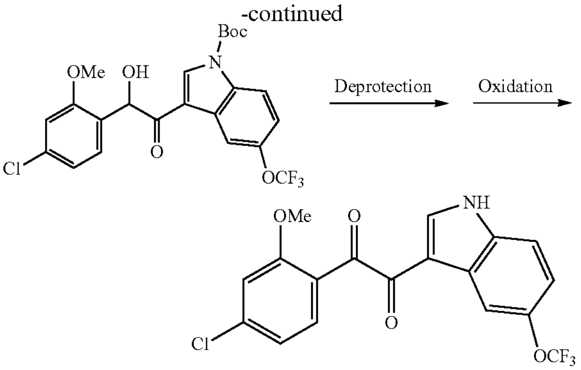

The process can comprise reacting 4-chloro-2-methoxybenzaldehyde with a N-protected 5-(Trifluoromethoxy)-1H-indole (for example tert-butyl 3-formyl-5-(trifluoromethoxy)indole-1-carboxylate), in the presence of a suitable catalyst such as 6,7-dihydro-2-pentafluorophenyl-5H-pyrrolo[2,1-c]-1,2,4-triazolium tetrafluoroborate or 3-benzyl-5-(2-hydroxyethyl)-4-methylthiazol-3-ium chloride and in the presence of a suitable base such as diisopropylethylamine (DIPEA) to yield tert-butyl 3-[2-(4-chloro-2-methoxy-phenyl)-2-hydroxy-acetyl]-5-(trifluoromethoxy) indole-1-carboxylate. The carboxylate can then be deprotected and the resulting compound oxidized to yield compound G.

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 4:

Scheme 4

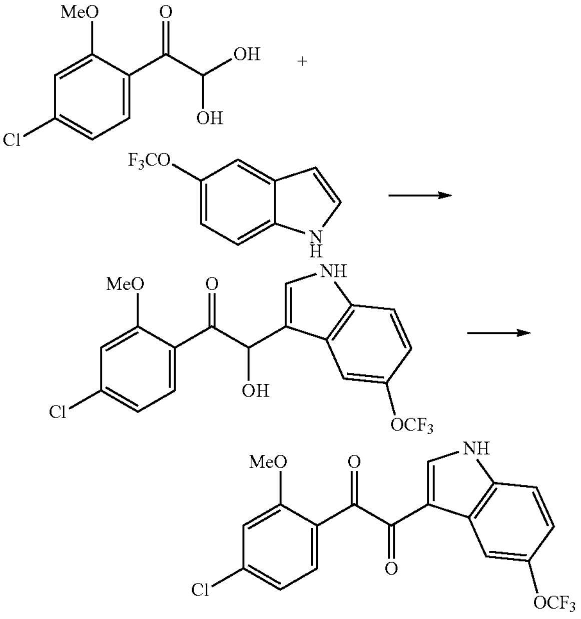

The process can comprise reacting 5-(trifluoromethoxy)-1H-indole with 1-(4-chloro-2-methoxy-phenyl)-2,2-dihydroxy-ethanone in the presence of a copper catalyst such as CuTC (TC=thiophene-2-carboxylate). The resulting 1-(4-chloro-2-methoxy-phenyl)-2-hydroxy-2-[5-(trifluoromethoxy)-1H-indol-3-yl]ethenone can then be oxidized in the presence of a suitable oxidizing agent to the corresponding compound G.

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 5:

Scheme 5

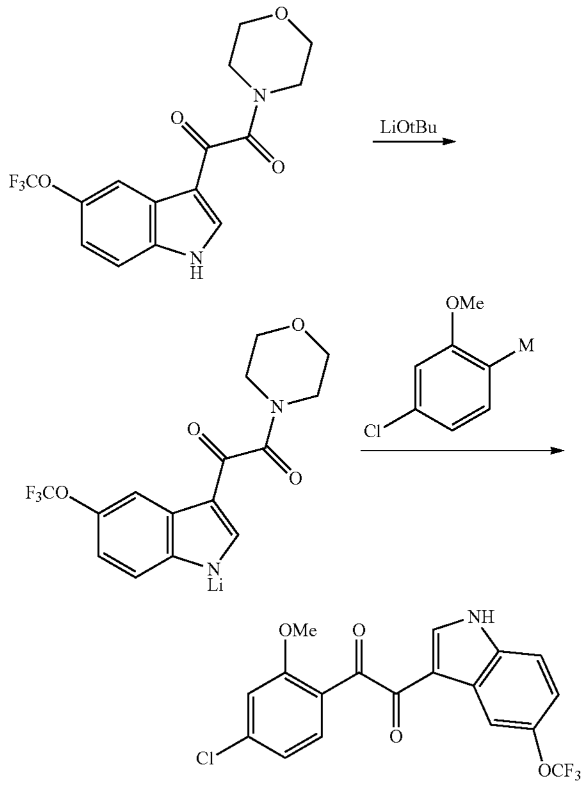

The process can comprise reacting 1-morpholine-2-(5-(trifluromethoxy)-1H-indol-3-yl)ethante-1,2-dione with LiOtBu. The resulting lithium 3-(2-morpholino-2-oxoacetyl)-5-(trifluoromethoxy)indol-1-ide can then be reacted with 4-chloro-2-methoxyphenyl halide (M can be bromide) in the presence of a suitable base such as butyl lithium to produce the corresponding compound G.

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 6:

Scheme 6

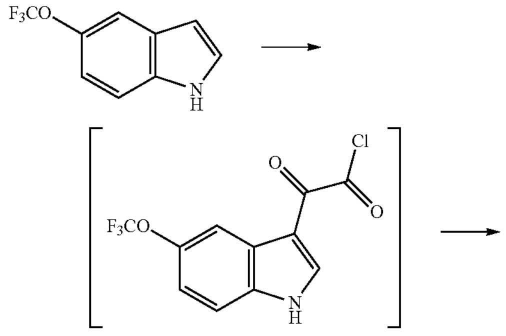

-continued

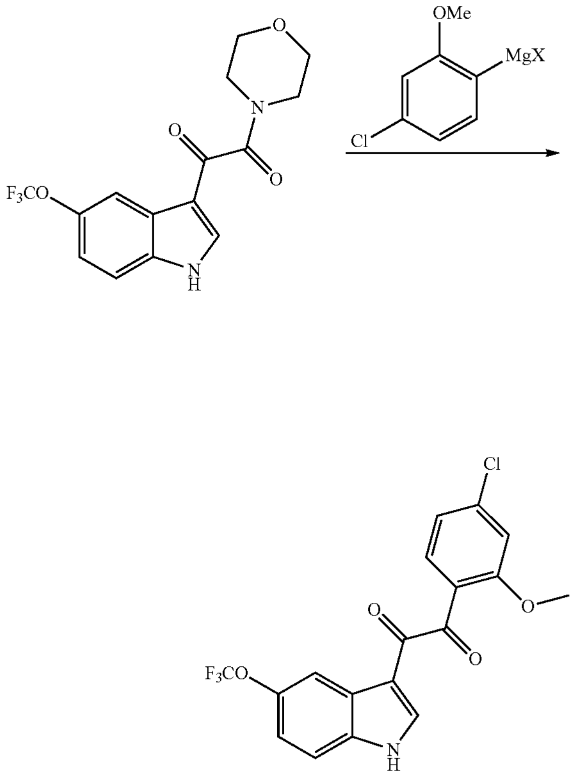

The process can comprise reacting 5-(trifluoromethoxy)-1H-indole with oxalyl chloride. This step can be performed in a suitable solvent such as methyl tert-butyl ether (MTBE). The resulting 2-oxo-2-(5-(trifluoromethoxy)-1H-indol-3-yl) acetyl chloride can then be reacted with morpholine to produce 1-morpholino-2-(5-(trifluoromethoxy)-1H-indol-3-yl)ethane-1,2-dione. This compound can then be reacted with 4-chloro-2-methoxyphenyl)magnesium halide (X can be Br) in the presence of a suitable base such as lithium bis(trimethylsilyl)amide (LiHMDS), to afford the corresponding compound G.

Alternatively, intermediate compound G (1-(4-chloro-2-methoxyphenyl)-2-(5-(trifluoromethoxy)-1H-indol-3-yl) ethane-1,2-dione) can be prepared as outlined in Scheme 7:

Scheme 7

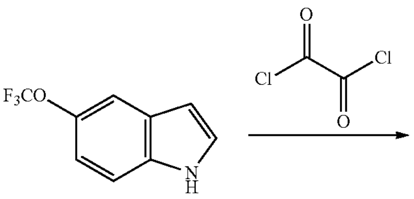

-continued

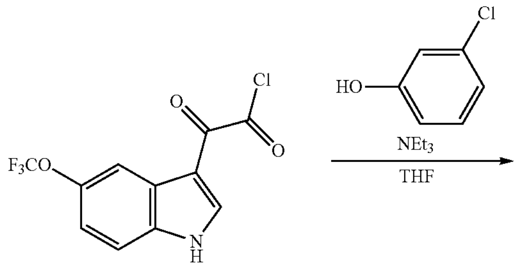

-continued

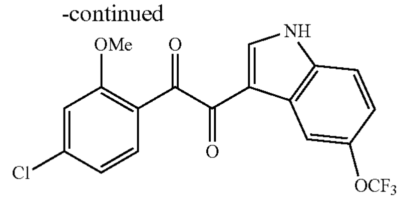

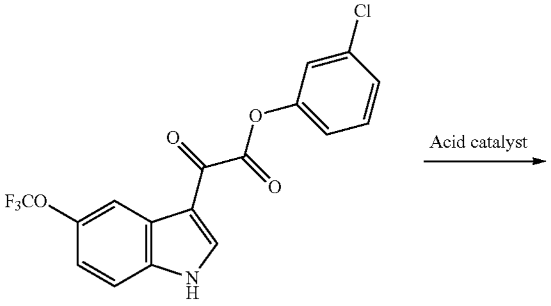

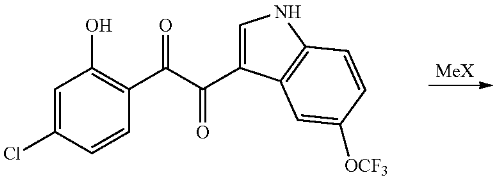

The process can comprise reacting 5-(trifluoromethoxy)-1H-indole with oxalyl chloride to give 2-oxo-2-[5-(trifluoromethoxy)-1H-indol-3-yl]acetyl chloride. This step can be performed in a suitable solvent such as methyl tert-butyl ether (MTBE). 2-oxo-2-[5-(trifluoromethoxy)-1H-indol-3-yl]acetyl chloride can then be reacted with 3-chlorophenol, preferably in the presence of a suitable base such as triethylamine to produce 1-(3-chlorophenyl)-2-[5-(trifluoromethoxy)-1H-indol-3-yl]ethane-1,2-dione. This step can be performed in a suitable solvent such as THF. Acid catalysis of the dione can give 1-(5-chloro-2-hydroxy-phenyl)-2-[5-(trifluoromethoxy)-1H-indol-3-yl]ethane-1,2-dione. Methylation of the OH group of 1-(5-chloro-2-hydroxy-phenyl)-2-[5-(trifluoromethoxy)-1H-indol-3-yl] ethane-1,2-dione, with for example methyl halide such as $CH_3I$ can provide intermediate compound G.

In some other embodiments, the process for the synthesis of (S)-2-(4-chloro-2-methoxyphenyl)-2-((3-methoxy-5-(methylsulfonyl)phenyl)amino)-1-(5-(trifluoromethoxy)-1H-indol-3-yl)ethanone can be performed as outlined in Scheme 8:

Scheme 8

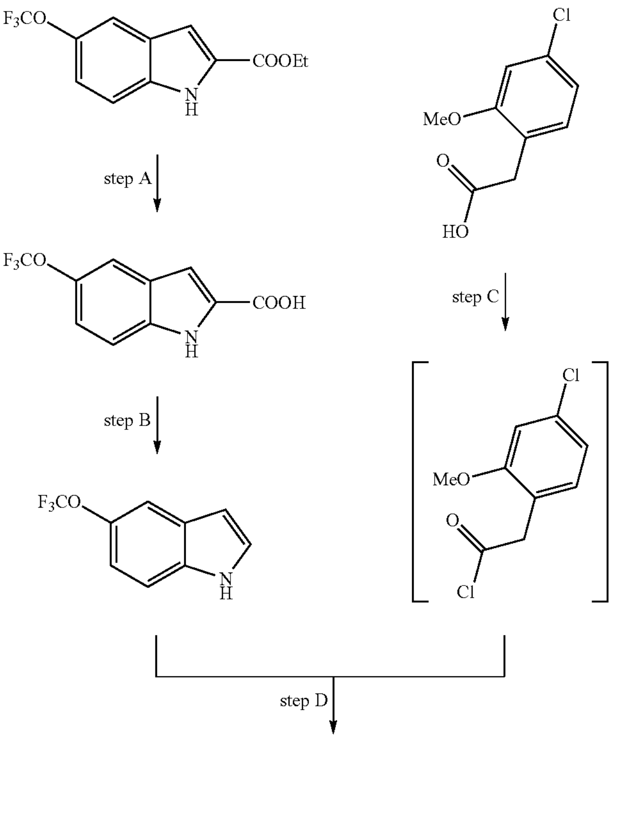

-continued
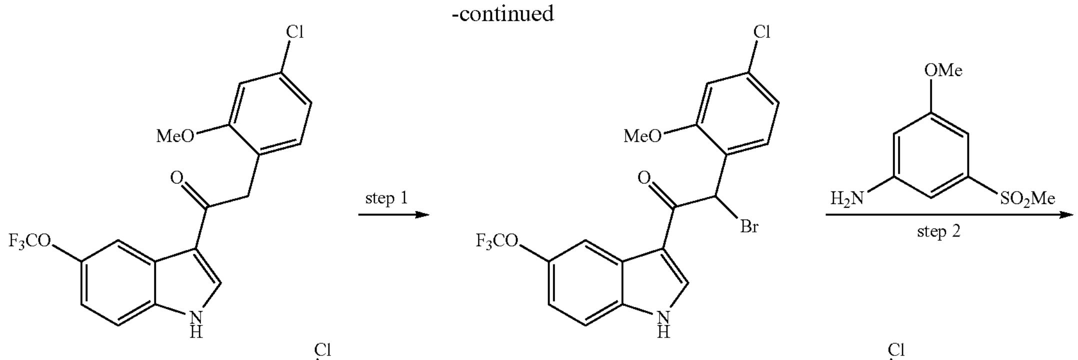
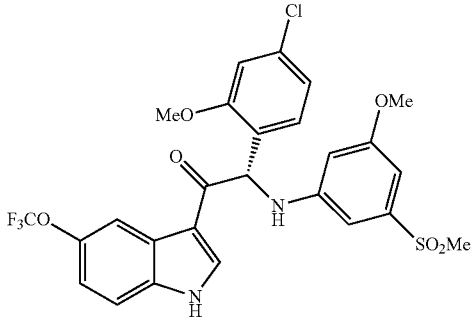
and
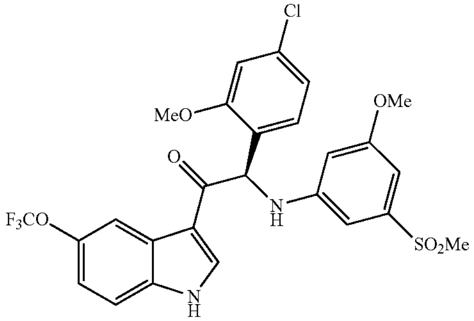
(1:1)
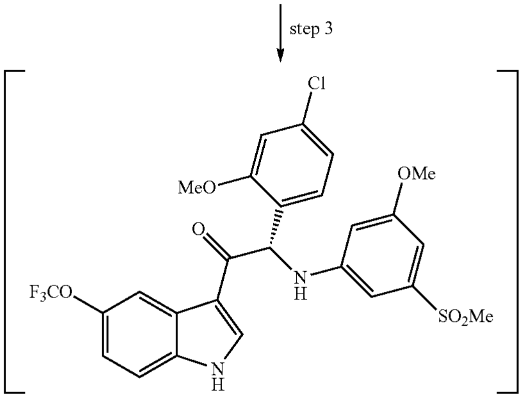
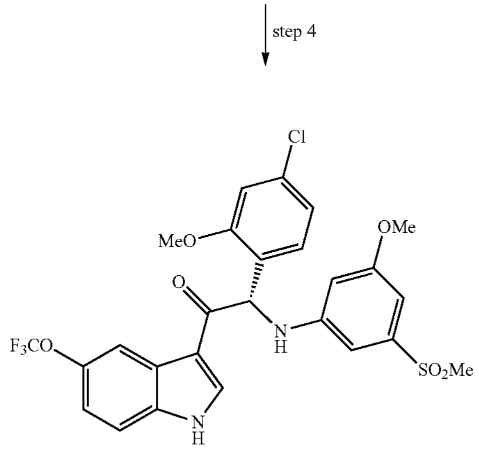
5-(trifluoromethoxy)-1H-indole can be prepared by hydrolysis of ethyl 5-(trifluoromethoxy)-1H-indole-2-carboxylate (step A) in the presence of a suitable base such as sodium hydroxide in methanol, followed by the decarboxylation of 5-(trifluoromethoxy)-1H-indole-2-carboxylic acid (step B) in the presence of suitable decarboxylating agents such as copper-quinoline. 2-(4-chloro-2-methoxyphenyl) acetyl chloride can be prepared from 2-(4-chloro-2-methoxyphenyl)acetic acid using a suitable chlorinating agent such thionyl chloride (step C), in a suitable solvent such as toluene. The reaction of the 2-(4-chloro-2-methoxyphenyl)acetyl chloride with 5-(trifluoromethoxy)-1H-indole (step D) can be performed using a suitable Lewis acid reagent such as for example $Et_2AlCl$, $AlCl_3$ or $TiCl_4$ in a suitable solvent like for example toluene, $CH_2Cl_2$ or 1,2-dichloroethane, to produce 2-(4-chloro-2-methoxyphenyl)-1-(5-(trifluoromethoxy)-1H-indol-3-yl)ethenone. This compound can be then brominated (step 1) with a suitable bromination agent such as phenyltrimethylammonium tribromide in a suitable solvent such as tetrahydrofuran. The resulting 2-bromo-2-(4-chloro-2-methoxyphenyl)-1-(5-(trifluoromethoxy)-1H-indol-3-yl)ethanone can be coupled with 3-methoxy-5-(methylsulfonyl)aniline (step 2) by means of a suitable phase transfer catalyst, such as tetrabutylammonium bromide in a mixture of solvents such as toluene and an aqueous buffer solution which can be made for example of sodium dihydrogen phosphate dihydrate and dipotassium hydrogen phosphate trihydrate. (S)-2-(4-chloro-2-methoxyphenyl)-2-((3-methoxy-5-(methylsulfonyl)phenyl)amino)-1-(5-(trifluoromethoxy)-1H-indol-3-yl)ethenone can then be obtained by chiral separation of the resulting mixture (steps 3 and 4). Chiral separation can be made for instance by means of chiral chromatography.

EXAMPLES

General. All reagents were commercially available and used without further purification unless otherwise stated. All reactions were performed under a nitrogen atmosphere unless otherwise stated. All reactions were monitored by HPLC method using Waters H-Class with UV detector or equivalent. All $^1H$ NMR and $^{13}C$ NMR spectra were recorded on a Bruker 400 or 500 MHz spectrometer using DMSO-d6 or $CDCl_3$ as the solvent.

Example 1. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone (D)

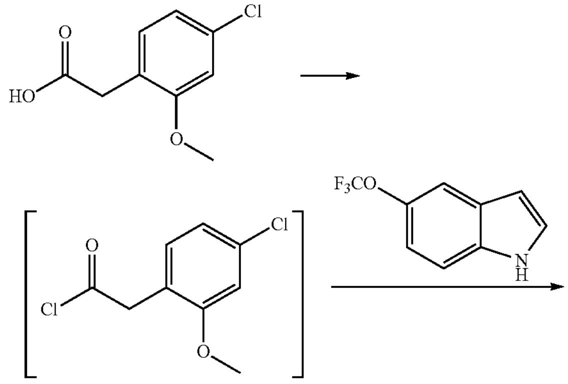

-continued

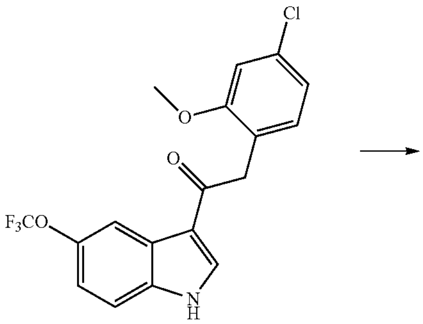

A

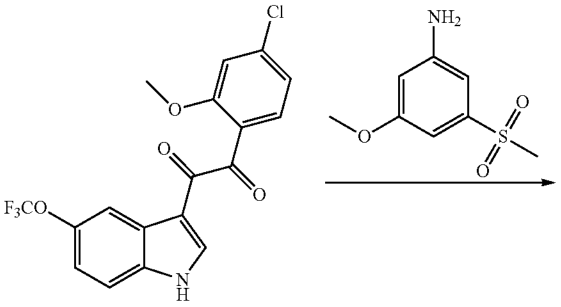

G

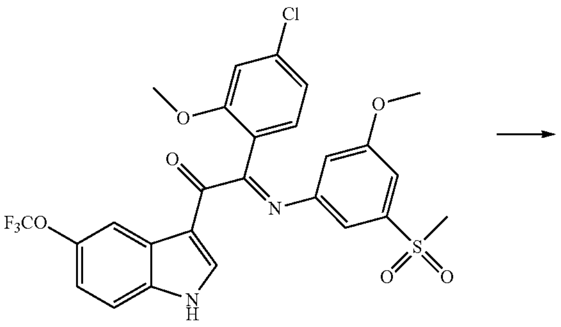

F

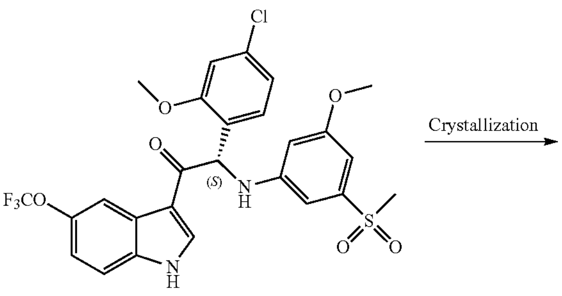

D

-continued

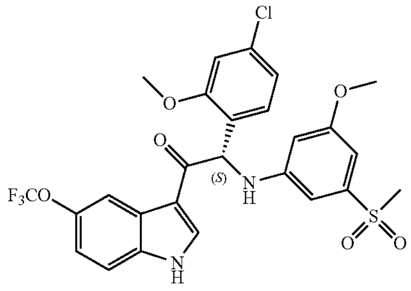

D

Step 1. Synthesis of 2-(4-chloro-2-methoxyphenyl)-1-(5-(trifluoromethoxy)-1H-indol-3-yl)ethenone (A)

(A)

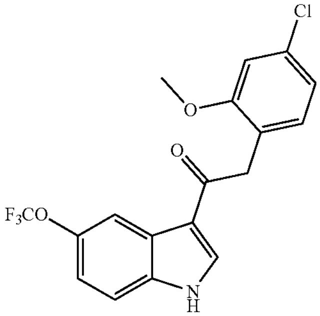

To a solution of 2-(4-chloro-2-methoxyphenyl)acetic acid (30 g, 150 mmol) in toluene (300 mL) at 20° C. was added thionyl chloride (21.4 g, 180 mmol). The solution was heated to 60° C. After the mixture was stirred for 16 h, the solution was concentrated under reduced pressure and solvent-switch with toluene (150 mL) twice. The solution was concentrated to give 2-(4-chloro-2-methoxyphenyl)acetyl chloride (113 g, 150 mmol) as a yellow solution. To a separate jacketed reactor was added 5-(trifluoromethoxy)-1H-indole (10 g, 50 mmol) and toluene (30 mL). The solution was cooled to −10° C., and a solution of diethyl aluminium chloride (0.9 M in toluene, 66 mL, 60 mmol) was added slowly to <−5° C. The reaction mixture was stirred below −5° C. for an hour, then the preceding prepared acyl chloride solution (50 g, 65 mmol) was added and stirred at −10° C. for another 16 h. The reaction mixture was quenched with $H_2O$ (100 mL) below −5° C., then tetrahydrofuran (THF) (200 mL) was added to extract. The organic phase was separated, and the organic layer was washed with $H_2O$ (100 mL). The organic phase was concentrated to ~20 mL under reduced pressure, then methylcyclohexane (100 mL) was added at 25° C. to precipitate out the solid. The mixture was filtered. The cake was dried to give product (A) (17.5 g, 45.2 mmol, 91% yield) as an off-white solid. $^1H$ NMR (400 MHz, DMSO-$d_6$) δ ppm 12.23 (br s, 1H), 8.58 (s, 1H), 8.04 (s, 1H), 7.59 (d, J=8.8 Hz, 1H), 7.25-7.17 (m, 2H), 1H) 7.06 (d, J=2.0 Hz, 1H), 6.98 (dd, J=8.0, 2.0 Hz, 1H), 4.18 (s, 2H), 3.75 (s, 3H).

Step 2. Synthesis of 1-(4-chloro-2-methoxyphenyl)-2-(5-(trifluoromethoxy)-1H-indol-3-yl)ethane-1,2-dione (G)

(G)

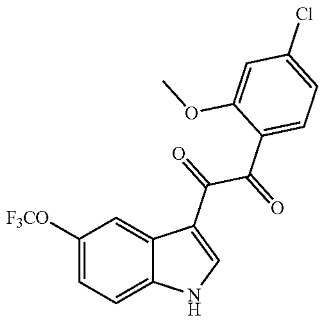

To a solution of 2-(4-chloro-2-methoxyphenyl)-1-(5-(trifluoromethoxy)-1H-indol-3-yl)ethanone (A) (800 g, 2085 mmol) in 2-Me-THF (8000 mL) at 20-30° C. was added dimethyl sulfoxide (DMSO) (651 g, 8338 mmol) and $I_2$ (1058 g, 4169 mmol) under ambient atmosphere. The solution was heated to 70° C. After the mixture was stirred for 20 h, the reaction mixture was quenched with 10% of $Na_2SO_3$ aqueous solution (8.0 L) at 45° C. and stirred for an hour. The organic phase was separated, and the organic layer was washed with 10% of $Na_2SO_4$ aqueous solution (8.0 L). The organic phase was concentrated to around 2.0 L under reduced pressure and heptane (8.0 L) was added drop-wise at 55° C. to precipitate out the solid. The mixture was cooled to 25° C. and stirred for another 14 hours. The mixture was filtered. The cake was dried to give product G (678 g, 1703 mmol, 82% yield) as a brown solid. $^1H$ NMR (400 MHz, DMSO-$d_6$) δ ppm 12.51 (br s, 1H), 8.24 (d, J=3.0 Hz, 1H), 8.04 (s, 1H), 7.84 (d, J=8.4 Hz, 1H), 7.67 (d, J=8.8 Hz, 1H), 7.38-7.21 (m, 3H), 3.62 (s, 3H), 3.62 (s, 3H), 3.62 (s, 3H), 3.36-3.25 (m, 1H)

Step 3. Synthesis of 2-(4-chloro-2-methoxyphenyl)-2-((3-methoxy-5-(methylsulfonyl)-phenyl)imino)-1-(5-(trifluoromethoxy)-1H-indol-3-yl)ethanone (F)

(F)

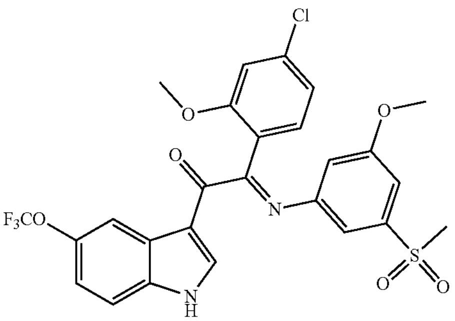

To a solution of 1-(4-chloro-2-methoxyphenyl)-2-(5-(trifluoromethoxy)-1H-indol-3-yl)ethane-1,2-dione (G) (20 g, 50.3 mmol) in 2-Me-THF (100 mL) and toluene (100 mL) at 20-30° C. were added 3-methoxy-5-(methylsulfonyl)aniline (10.1 g, 50.3 mmol) and $Zn(OTf)_2$ (9.1 g, 25.1 mmol). The reaction mixture was heated to reflux with a Dean-Stark.

After the mixture was stirred for 20 h, the reaction mixture was diluted with 2-Me-THF (200 mL) and quenched with $Et_3N$ (10.5 mL, 75.4 mmol) at 20° C. Then $H_2O$ (200 mL) was added and stirred for an hour. The mixture was filtered and the filtrate was separated, and then the organic layer was washed with $H_2O$ (100 mL). The organic layer was concentrated to 20 mL under reduced pressure and chased with isopropyl alcohol (IPA) (100 mL). After the mixture was concentrated to 20 mL, another portion of IPA (120 mL) was added. The mixture was added $H_2O$ (60 mL) at 60° C. to precipitate out the solid. The mixture was cooled to 25° C. and stirred for 10 hours. The mixture was filtered. The cake was dried to give product (F) (25.1 g, 41.7 mmol, 83% yield) as an off-white solid. $^1H$ NMR (400 MHz, $CDCl_3$) δ ppm 9.26 (s, 2H), 9.21 (s, 1H), 8.35 (d, J=1.8 Hz, 2H), 8.27 (s, 1H), 7.97 (br s, 1H), 7.89 (d, J=8.5 Hz, 1H), 7.40 (br s, 1H), 7.34 (d, J=8.8 Hz, 2H), 7.15-7.22 (m, 2H), 7.00-7.12 (m, 5H), 6.86-6.94 (m, 5H), 6.71-6.83 (m, 4H), 6.54-6.63 (m, 2H), 3.70 (s, 5H), 3.61-3.52 (m, 8H), 3.41 (s, 3H), 2.83 (s, 5H), 2.70 (s, 3H), 1.36 (br s, 1H), 1.27-1.01 (m, 5H), 0.97-0.69 (m, 3H)

Step 4. Synthesis of (S)-2-(4-chloro-2-methoxyphenyl)-2-((3-methoxy-5-(methylsulfonyl)-phenyl) amino)-1-(5-(trifluoromethoxy)-1H-indol-3-Yl)ethanone (D)

(D)

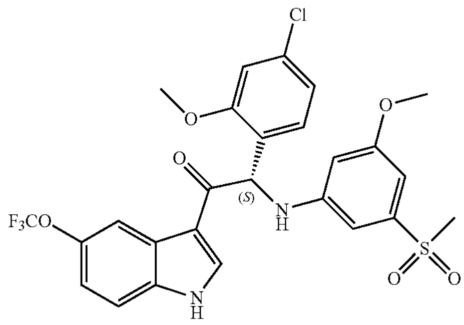

To a $N_2$ flushed 500 mL hydrogenation flask were added 2-(4-chloro-2-methoxyphenyl)-2-((3-methoxy-5-(methylsulfonyl)phenyl)imino)-1-(5-(trifluoromethoxy)-1H-indol-3-yl)ethanone (F) (20 g, 34.4 mmol), bis(norbornadiene) rhodium(I) tetrafluoroborate (38.6 mg, 103 μmol) and (S)-1-[(RP)-2-(diphenylphosphino)ferrocenyl]ethyldi-tert-butylphosphine (57 mg, 103 μmol) in degassed THF (200 mL). The reaction mixture was evacuated and backfilled with $N_2$ and $H_2$ three times respectively. The reaction mixture was heated to 50° C. under 3 bar $H_2$ pressure. After stirring for 16 h, silica thiol (2.0 g, 10% wt %) was added to the reaction mixture and it was stirred for another 16 h at 50° C. The reaction mixture was filtered through a pad of Celite. Then the filtrate was added heptane (200 mL) drop-wise at 40° C. and stirred for 16 h. The resulting suspension was filtered to remove solid impurities and the filtrate was concentrated under reduced pressure to give crude D (20 g) as an off-white solid. To a separate jacketed reactor was added crude D (10 g) and MeOH (63 mL). The mixture was heated to 64° C. and stirred for 0.5 hour to a clear solution. Then the solution was cooled to 45° C. linearly and seed of the product was added (2 wt %). The mixture was aged for 3 h and $H_2O$ was added (21 mL) drop-wise at 45° C. Then the mixture was cooled to 25° C. and stirred for another 8 h. The mixture was filtered. The cake was dried to give product D (7.6 g, 13 mmol, 76% yield) as an off-white solid. $^1H$ NMR (400 MHz, DMSO-$d_6$) δ ppm 12.32 (br d, J=2.6 Hz, 1H), 8.56 (d, J=3.3 Hz, 1H), 8.08 (s, 1H), 7.60 (d, J=8.8 Hz, 1H), 7.37 (d, J=8.3 Hz, 1H), 7.28-7.18 (m, 1H), 7.18-7.06 (m, 2H), 6.99 (dd, J=8.3, 1.9 Hz, 1H), 6.92 (s, 1H), 6.68-6.52 (m, 2H), 6.27 (br d, J=7.6 Hz, 1H), 4.00 (s, 3H), 3.73 (s, 3H), 3.10 (s, 3H).

Example 1a. Synthesis of (S)-2-(4-chloro-2-methoxyphenyl)-2-((3-methoxy-5-(methylsulfonyl) phenyl)amino)-1-(5-(trifluoromethoxy)-1H-indol-3-yl)ethenone (D)

A vial under nitrogen was charged with 2.3 mg Ru(COD)$(TFA)_2$, 3.7 mg (S)-DM-SEGPHOS and 0.5 mL anhydrous 1,2-DCE. The solution was stirred for 30 minutes at 70° C. The reactor under nitrogen was charged with 1 gram of 2-(4-chloro-2-methoxyphenyl)-2-((3-methoxy-5-(methylsulfonyl)phenyl)imino)-1-(5-(trifluoromethoxy)-1H-indol-3-yl)ethanone (F) and 20 mL anhydrous THF and stirred until everything was dissolved. The catalyst solution was cooled down to 25° C. and added to the solution with compound (F). The nitrogen atmosphere was exchanged for 10 bar hydrogen and the reaction was warmed up to 50° C. After 2 hours, the reaction was completed as was determined by UPLC analysis. The product in solution was 48.2% ee. The solution was cooled down to ambient temperature and concentrated to 9 mL. Stirring at 25° C., 9 mL heptane was slowly charged to the reaction and a precipitate was formed. Filtration over glass filter, followed by washing with 5 mL heptane afforded the racemate in 427 mg (42.6% yield, 2.6% ee. Evaporation of the mother liquor and drying in the oven at 50° C. under reduced pressure afforded 372 mg (37.0% yield, 99.9% ee) of (S)-2-(4-chloro-2-methoxyphenyl)-2-((3-methoxy-5-(methylsulfonyl)phenyl)-amino)-1-(5-(trifluoromethoxy)-1H-indol-3-yl)ethanone (D).

Example 2. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone: Alternate Synthesis of Compound G Step 1. Synthesis of 2-oxo-2-(5-(trifluoromethoxy)-1H-indol-3-yl)acetyl chloride

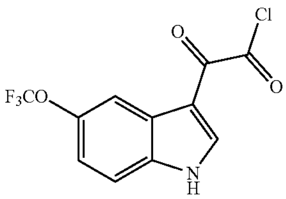 [SMILES: O=C(Cl)C(=O)c1c[nH]c2ccc(OC(F)(F)F)cc12]

A solution of 20 gram of 5-(trifluoromethoxy)-1H-indole (99.4 mmol) in 60 mL dry methyl tert-butyl ether (MTBE) was cooled to 0° C. Oxalyl chloride (10.4 mL, 119.3 mmol, 1.2 equiv.) was added dropwise over 5 minutes and the solution was warmed up to 20° C. After stirring for 1 hour, 20 mL heptane were added, and a yellow precipitate was formed. The mixture was stirred for another 10 minutes at 0° C. after which it was filtered on a glass filter (pore size 3).

The filter cake was washed with 40 mL of heptane and dried under vacuum at 50° C. for 2 hours. The product was obtained as a yellow solid that was sensitive to moisture (26.3 gram, 90.2 mmol, 91% yield). $^1$H NMR (THF-$d_8$, 400 MHz) δ ppm 11.77 (s, 1H), 8.48 (d, J=3.4 Hz, 1H), 8.34-8.06 (m, 1H), 7.56 (d, J=8.8 Hz, 1H), 7.24 (ddd, J=8.8, 2.4, 1.0 Hz, 1H). $^{13}$C NMR (THF-$d_8$, 101 MHz) δ 172.8, 169.1, 146.6, 140.2, 136.6, 128.1, 122.0 (q, J=254.7 Hz, $CF_3$), 119.1, 115.2, 114.5, 112.1.

Step 2. Synthesis of 1-morpholino-2-(5-(trifluoromethoxy)-1H-indol-3-yl)ethane-1,2-dione

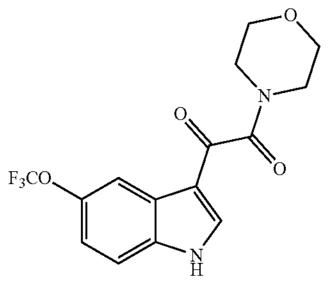 [SMILES: O=C(C(=O)N1CCOCC1)c1c[nH]c2ccc(OC(F)(F)F)cc12]

A solution of 15.7 gram morpholine (178.3 mmol, 2.0 equiv.) in 100 mL dry THF was cooled to 0° C. A solution of 26.0 gram 2-oxo-2-(5-(trifluoromethoxy)-1H-indol-3-yl) acetyl chloride (89.1 mmol) in 100 mL THF was added dropwise over 1 hour while maintaining the temperature below 5° C. After the addition was complete, the reaction was stirred for another 30 minutes at 0° C. before 780 mL water was added dropwise over 30 minutes. The white precipitate that was filtered and washed with 130 mL sat. aq. $NaHCO_3$ and 100 mL of water. The product was dried under vacuum at 50° C. for 18 hours. The product was obtained as a white solid (28.2 gram, 89.2 mmol, 92% yield). $^1$H-NMR (DMSO, 400 MHz) δ ppm 12.57 (s, 1H), 8.36 (s, 1H), 8.01 (d, J=2.3 Hz, 1H), 7.65 (d, J=8.8 Hz, 1H), 7.28 (dd, J=8.8, 2.4 Hz, 1H), 3.71 (t, J=4.7 Hz, 2H), 3.62 (t, J=4.7 Hz, 2H), 3.52 (t, J=4.7 Hz, 2H), 3.36 (t, J=4.8 Hz, 2H). $^{13}$C-NMR (DMSO, 101 MHz) δ ppm 186.0, 165.4, 144.3 (q, J=2.2 Hz), 135.4, 125.3, 120.3 (q, J=254.4 Hz, $CF_3$) 116.5, 66.2, 65.9, 46.0, 41.1.

Step 3. Synthesis of 4-chloro-2-methoxyphenyl)magnesium Bromide

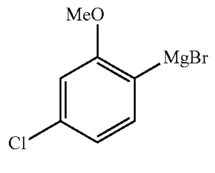

To a suspension of 583.3 mg magnesium turnings (24 mmol, 1.2 equiv.) in 30 mL THF was added 0.07 mL of diisobutylaluminium hydride (DiBAL-H) (1.0M in THF, 2 mol %) at 20° C. The solution was warmed up to 40° C. and a solution of 4.4 g 4-chloro-2-methoxyphenyl bromide in 7.2 mL THF (total volume of 10 mL) was added dropwise over 1 hour. The reaction was stirred for another 30 minutes at 40° C. before it was cooled down to 20° C. Titration with iodine determined a concentration of 0.44M.

Step 3 bis. Synthesis of 4-chloro-2-methoxyphenyl)magnesium Bromide

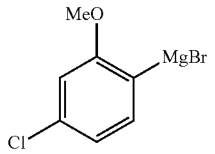

To a solution of 3 g 4-chloro-2-methoxyphenyl bromide in 15 mL THF, 8.7 mL of a 3M solution of isopropyl magnesium bromide in MeTHF was added at 40° C. over one hour. The reaction was stirred for another 16 hours at 40° C. before it was cooled down to 20° C. Titration with iodine determined a concentration of 0.46M.

Step 4. Synthesis of 1-(4-chloro-2-methoxyphenyl)-2-(5-(trifluoromethoxy)-1H-indol-3-yl)ethane-1,2-dione

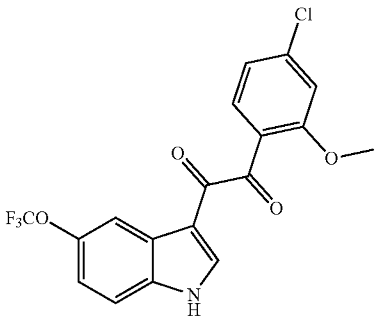 [SMILES: COc1cc(Cl)ccc1C(=O)C(=O)c1c[nH]c2ccc(OC(F)(F)F)cc12]

A solution of 5 gram 1-morpholino-2-(5-(trifluoromethoxy)-1H-indol-3-yl)ethane-1,2-dione (14.5 mmol) in 25 mL THF was cooled down to 0° C. A 1M solution of lithium bis(trimethylsilyl)amide (LiHMDS) (15.9 mL, 1.1 equiv.) was added dropwise over 15 minutes and the mixture was stirred for an additional 15 minutes at 0° C. A solution of (4-chloro-2-methoxyphenyl)magnesium bromide in THF (0.44M, 36.3 mL, 1.1 equiv.) was added dropwise over 30 minutes. The reaction was warmed up to 25° C. and stirred overnight before quenching with 50 mL 1M HCl. The phases were separated, and the aqueous layer was extracted with 25 mL MeTHF. Combined organic layers were dried on MgSO4, filtered, and concentrated in vacuo to 10-15 mL. The solution was warmed up and stirred 60° C. before adding 50 mL heptane. The mixture was stirred at 60° C. for 1 hour before slowly cooling down to 20° C. The solid was filtered off and the cake was washed with 20 mL heptane. The product was dried under vacuum at 50° C. for 18 hours. The product was obtained as a yellow solid (4.7 gram, 11.8 mmol, 81% yield). $^1$H-NMR (DMSO, 400 MHz) δ ppm 12.51 (s, 1H), 8.24 (d, J=3.2 Hz, 1H), 8.03 (t, J=1.9 Hz, 1H), 7.83 (d, J=8.3 Hz, 1H), 7.65 (dd, J=8.8, 0.5 Hz, 1H), 7.33 (d, J=1.9 Hz, 1H), 7.29 (dd, J=8.8, 1.6 Hz, 1H), 7.24 (dd, J=8.3, 1.9 Hz, 1H), 3.61 (s, 3H). $^{13}$C-NMR (DMSO, 101 MHz) δ ppm 192.6, 187.5, 160.4, 144.1 (q, J=2.3 Hz), 140.6, 138.3, 135.3, 131.9, 125.8, 122.7, 121.5, 121.0 (q, J=255.6 Hz, $CF_3$), 117.2, 114.1, 113.7, 112.9, 111.7, 56.8. Compound (S)-2-(4-chloro-2-methoxyphenyl)-2-((3-methoxy-5-(methylsulfonyl)phenyl)-amino)-1-(5-(trifluoromethoxy)-1H-indol-3-yl)ethenone (D) was prepared following steps 3 and 4 as disclosed in Example 1.

Example 3. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone: Alternate Synthesis of Compound G

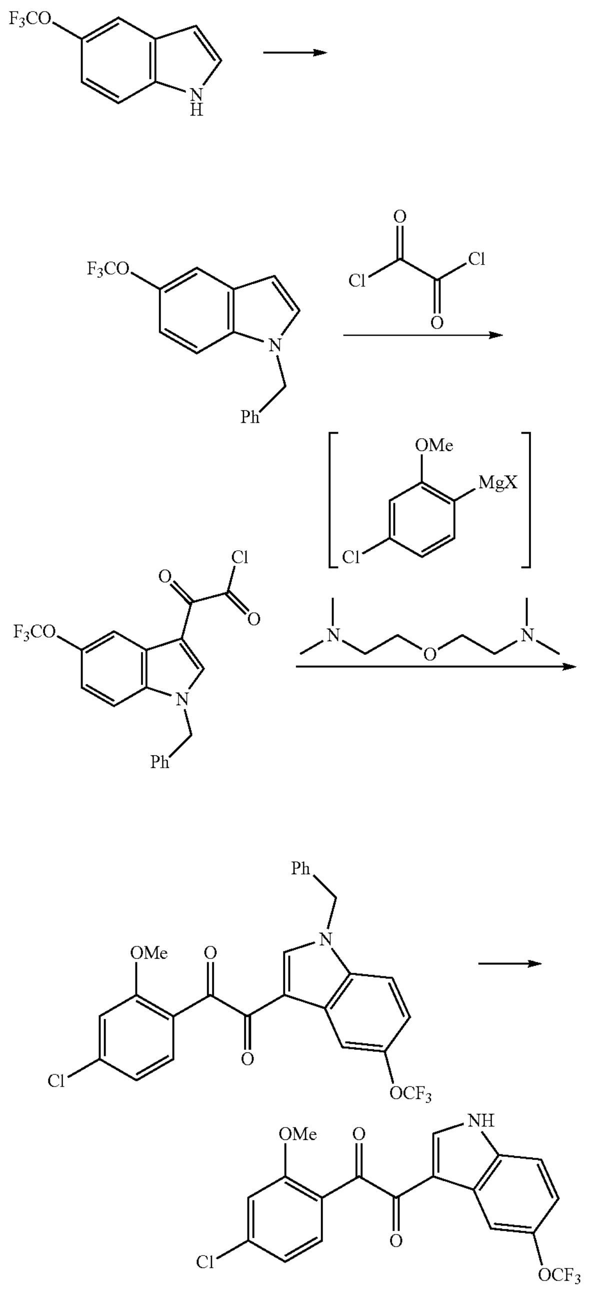

Compound G

Step 1. Synthesis of 1-benzyl-5-(trifluoromethoxy)-1H-indole

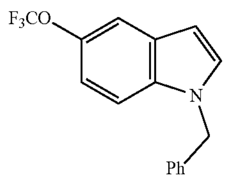 [SMILES: FC(F)(F)Oc1ccc2c(ccn2Cc2ccccc2)c1]

A solution of 10 gram of 5-(trifluoromethoxy)-1H-indole (49.7 mmol) in 70 mL THF was cooled down to 0° C. KOtBu (5.85 g, 52.2 mmol, 1.05 equivalent) was added followed by benzyl bromide (6.2 mL, 52.2 mmol, 1.05 equivalent) dropwise. The mixture was stirred at 0° C. for 30 minutes before slowly warming up to 20° C. and stirring at this temperature for 2 hours. A saturated solution of sodium carbonate (30 mL) was added and the phases separated. The organic layer was dried over $MgSO_4$ and concentrated to under reduced pressure to a reddish oil that was used without further purification (15.1 g, 89 area % purity by HPCL analysis).

Step 2. Synthesis of 2-(1-benzyl-5-(trifluoromethoxy)-1H-indol-3-yl)-2-oxoacetyl Chloride

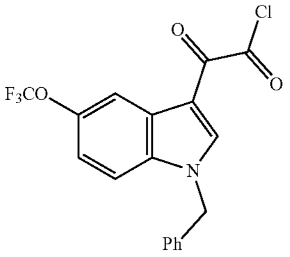 [SMILES: O=C(Cl)C(=O)c1cn(Cc2ccccc2)c2ccc(OC(F)(F)F)cc12]

A solution of 3 g of 1-benzyl-5-(trifluoromethoxy)-1H-indole (9.1 mmol) in diethyl ether (15 mL) was cooled to 0° C. Oxalyl chloride (1.4 g, 11 mmol, 1.2 equivalent) was added dropwise. The mixture was warmed up to 20° C. and stirred for one hour at this temperature. Heptane (45 mL) was added and the resulting yellow solid was filtered and washed with 20 mL of heptane. 2-(1-benzyl-5-(trifluoromethoxy)-1H-indol-3-yl)-2-oxoacetyl chloride was isolated as a yellow crystalline solid (2.47 g, 9.1 mmol, 65% yield) and used without further purification.

Step 3. Synthesis of 1-(1-benzyl-5-(trifluoromethoxy)-1H-indol-3-yl)-2-(4-chloro-2-methoxyphenyl)ethane-1,2-dione

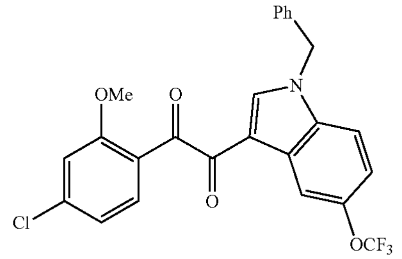 [SMILES: COc1cc(Cl)ccc1C(=O)C(=O)c1cn(Cc2ccccc2)c2ccc(OC(F)(F)F)cc12]

2-(1-benzyl-5-(trifluoromethoxy)-1H-indol-3-yl)-2-oxoacetyl chloride (2 g, 5.24 mmol) was dissolved in THF (10 mL) and cooled down to 0° C. A mixture of (4-chloro-2-methoxyphenyl)magnesium bromide in THF (0.44M, 12 mL, 1.1 equiv.) and 2-(Dimethylamino)ethyl ether (1.15 mL, 6.02 mmol, 1.15 equivalent) was added dropwise over 30 minutes. HCl (6M, 15 mL) was added and the mixture warmed up to 20° C. The two phases were separated and the aqueous layer extracted twice with ethyl acetate (15 mL each). The combined organic layers were dried over MgSO4, concentrated to dryness and purified by chromatography to afford 2.51 g of 1-(1-benzyl-5-(trifluoromethoxy)-1H-indol-3-yl)-2-(4-chloro-2-methoxyphenyl) ethane-1,2-dione (3.77 mmol, 72% yield) as an orange oil.

Compound (S)-2-(4-chloro-2-methoxyphenyl)-2-((3-methoxy-5-(methylsulfonyl)phenyl)-amino)-1-(5-(trifluoromethoxy)-1H-indol-3-yl)ethenone (D) was prepared following steps 3 and 4 as disclosed in Example 1.

Example 4. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone, Alternate Synthesis of Compound G

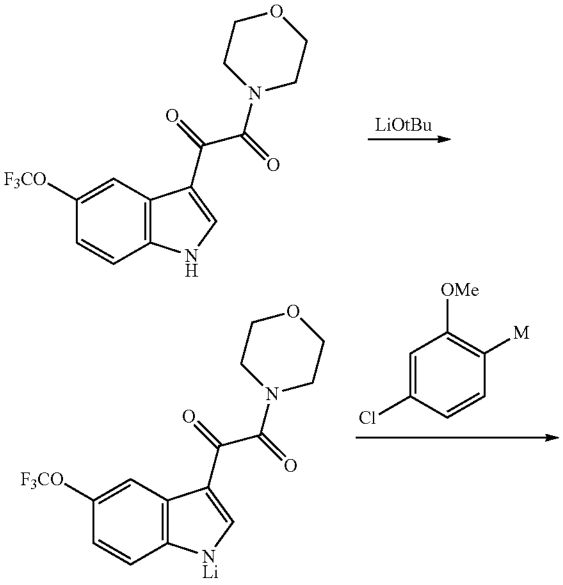

-continued

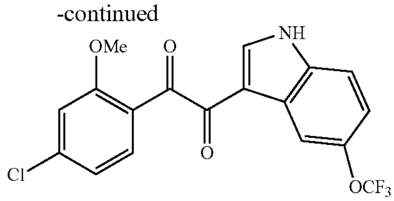

Step 1. Synthesis of lithium 3-(2-morpholino-2-oxoacetyl)-5-(trifluoromethoxy)indol-1-ide

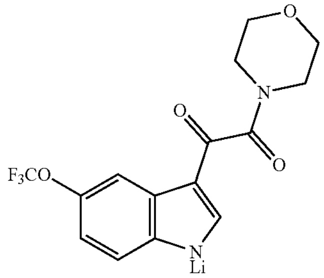

A solution of 10 g of 1-morpholine-2-(5-(trifluromethoxy)-1H-indol-3-yl)ethante-1,2-dione (29.2 mmol) in 50 mL THF was cooled down to 0° C. To this solution, 2.34 g (29.21 mmol, 1 equivalent) of LiOtBu was added. The reaction mixture was warmed up to 20° C. over 30 minutes, then 20 mL of toluene were added, and the mixture stirred for 30 minutes and the solid formed filtered and dried at 50° C. under reduced pressure to obtain 10.5 g of lithium 3-(2-morpholino-2-oxoacetyl)-5-(trifluoromethoxy)-indol-1-ide that was used without further purification.

Step 2. Synthesis of 1-(4-chloro-2-methoxyphenyl)-2-(5-(trifluoromethoxy)-1H-indol-3-yl)ethane-1,2-dione

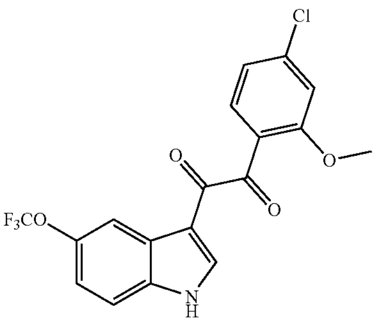 [SMILES: COc1cc(Cl)ccc1C(=O)C(=O)c1c[nH]c2ccc(OC(F)(F)F)cc12]

A suspension of 5 g of lithium 3-(2-morpholino-2-oxoacetyl)-5-(trifluoromethoxy)indol-1-ide (14.4 mmol) and 5.1 g 4-chloro-2-methoxyphenyl bromide (23 mmol, 1.6 equivalent) in 70 mL anhydrous THF was cooled to 0° C. 8.6 mL of a 2.5M solution of butyl lithium in hexane (21.5 mmol, 1.5 equivalents) were added dropwise over 2 hours. After warming up to 20° C., 15 ml of 2M aqueous hydrochloric acid was added dropwise. The layers were separated, and the aqueous phase extracted twice with 10 mL of MeTHF. The combined organic layers were dried and concentrated under reduced pressure to a brown solid that was purified by chromatography using heptane EtOAc mixtures. The product was obtained as a yellow solid (3.6 gram, 9.1 mmol, 63% yield). $^1$H-NMR (DMSO, 400 MHz) δ ppm 12.51 (s, 1H), 8.24 (d, J=3.2 Hz, 1H), 8.03 (t, J=1.9 Hz, 1H), 7.83 (d, J=8.3 Hz, 1H), 7.65 (dd, J=8.8, 0.5 Hz, 1H), 7.33 (d, J=1.9 Hz, 1H), 7.29 (dd, J=8.8, 1.6 Hz, 1H), 7.24 (dd, J=8.3, 1.9 Hz, 1H), 3.61 (s, 3H). $^{13}$C-NMR (DMSO, 101 MHz) δ ppm 192.6, 187.5, 160.4, 144.1 (q, J=2.3 Hz), 140.6, 138.3, 135.3, 131.9, 125.8, 122.7, 121.5, 121.0 (q, J=255.6 Hz, $CF_3$), 117.2, 114.1, 113.7, 112.9, 111.7, 56.8.s Compound (S)-2-(4-chloro-2-methoxyphenyl)-2-((3-methoxy-5-(methylsulfonyl)phenyl)-amino)-1-(5-(trifluoromethoxy)-1H-indol-3-yl)ethenone (D) was prepared following steps 3 and 4 as disclosed in Example 1.

Example 5. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone, Alternate Synthesis of Compound G

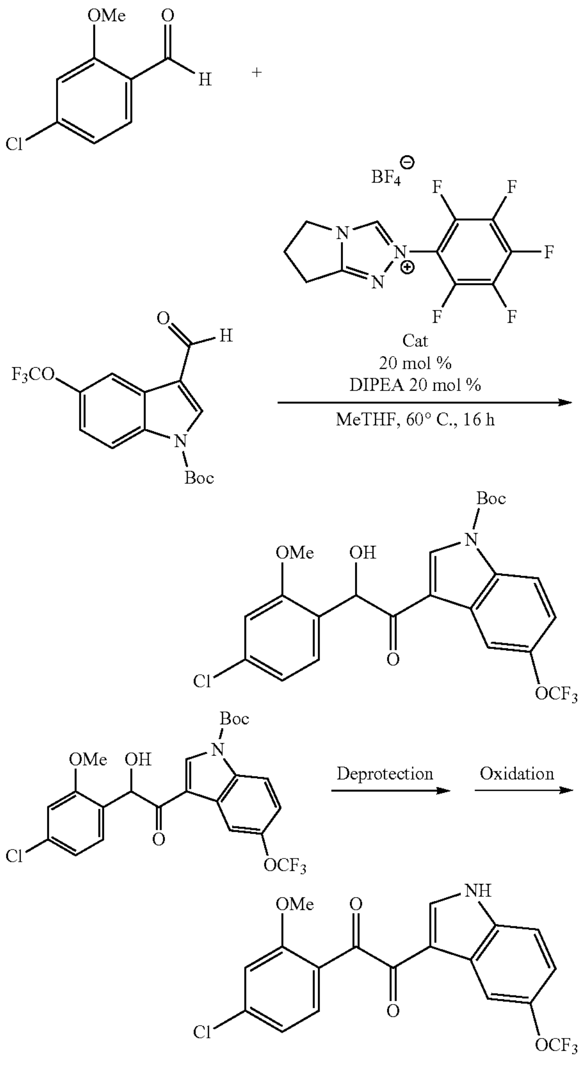

To a solution of 6,7-dihydro-2-pentafluorophenyl-5H-pyrrolo[2,1-c]-1,2,4-triazolium tetrafluoroborate (42.5 mg, 0.12 mmol, 0.2 equiv.) in acetonitrile was added diisopropylethylamine (20 μl, 0.12 mmol, 0.2 equiv.) and the mixture was stirred for 15 minutes at 25° C. To this, a solution of 4-chloro-2-methoxybenzaldehyde (100 mg, 0.59 mmol) and tert-butyl 3-formyl-5-(trifluoromethoxy)indole-1-carboxylate (193.0 mg, 0.59 mmol, 1 equiv.) in acetonitrile. The reaction was warmed up to 60° C. and stirred for 20 hours. After cooling down to 20° C., water was added, and the precipitate was collected by filtration. The filter cake was washed with water and dried at 40° C. under vacuum to afford the product as a white solid (121 mg, 0.24 mmol, 410% yield). $^1$H-NMR (400 MHz, $CDCl_3$) δ ppm 8.32 (s, 1H), 8.25 (s, 1H), 8.08 (d, J=9.1 Hz, 1H), 7.22 (m, 2H), 6.92 (m, 2H), 6.06 (d, J=5.5 Hz, 1H), 4.59 (d, J=5.7 Hz, 1H) 3.94 (s, 3H), 1.72 (s, 1H, OH), 1.68 (s, 9H). $^{13}$C NMR (101 MHz, $CDCl_3$) δ ppm 194.2, 157.0, 148.5, 146.4, 146.4, 135.6, 134.4, 133.6, 129.8, 128.6, 127.3, 121.8, 119.4, 116.2, 115.8, 115.1, 112.5, 86.3, 70.2, 56.3, 28.2.

Compound (S)-2-(4-chloro-2-methoxyphenyl)-2-((3-methoxy-5-(methylsulfonyl)phenyl)amino)-1-(5-(trifluoromethoxy)-1H-indol-3-yl)ethenone (D) was prepared following steps 3 and 4 as disclosed in Example 1

Example 6. Synthesis of a Compound of Formula (I): (S)-2-(4-chloro-2-methoxy-phenyl)-2-((3-methoxy-5-(methylsulfonyl)phenyl)amino)-1-(5-(trifluoromethoxy)-1H-indol-3-yl)ethenone, Alternate Synthesis of Compound G

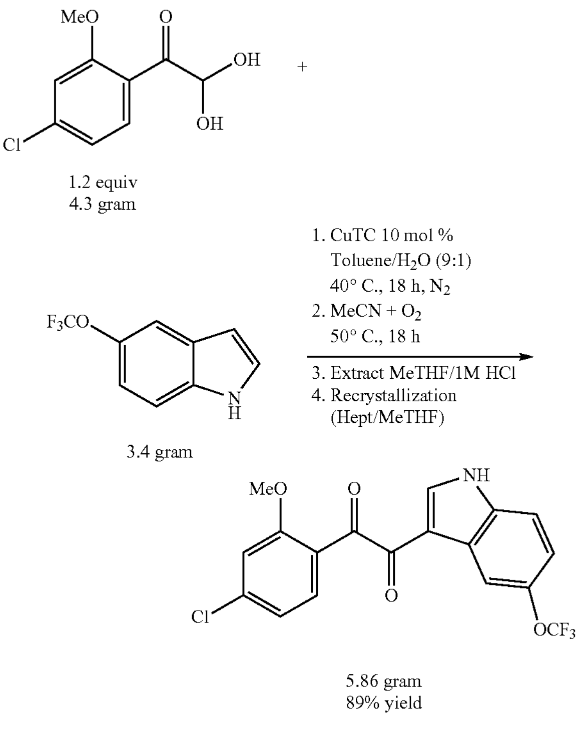

A vial with 5-(trifluoromethoxy)-1H-indole (3.4 gram, 17 mmol), 4-chloro-2-methoxy-phenylglyoxal hydrate (4.3 gram, 20 mmol, 1.2 equiv.) and copper(I) thiophene-2-carboxylate (165 mg, 0.85 mmol, 5 mol %) was placed under nitrogen atmosphere. Toluene (34 mL) and water (3.4 mL) were added to this and the reaction mixture was heated to 40° C. for 18 hours. The septum was removed, and acetonitrile (10 mL) was added. The reaction was heated 50° C. for 18 hours under ambient atmosphere and filtered over celite. 2-methyl tetrahydrofuran (30 mL) and 1M HCl (30 mL) were added, and the layers were separated. The aqueous layer was extracted with 2-methyl tetrahydrofuran and the combined organic layers were dried on $MgSO_4$, filtered, and concentrated in vacuo to 5-10 mL. The solution was warmed up and stirred 60° C. before adding 20 mL heptane. The mixture was stirred at 60° C. for 1 hour before slowly cooling down to 20° C. The solid was filtered off and the cake was washed with 10 mL heptane. The product was dried under vacuum at 50° C. for 18 hours. The product was obtained as a yellow solid (5.8 gram, 15.1 mmol, 89% yield). $^{1}$H-NMR (DMSO, 400 MHz) δ ppm 12.51 (s, 1H), 8.24 (d, J=3.2 Hz, 1H), 8.03 (t, J=1.9 Hz, 1H), 7.83 (d, J=8.3 Hz, 1H), 7.65 (dd, J=8.8, 0.5 Hz, 1H), 7.33 (d, J=1.9 Hz, 1H), 7.29 (dd, J=8.8, 1.6 Hz, 1H), 7.24 (dd, J=8.3, 1.9 Hz, 1H), 3.61 (s, 3H). $^{13}$C-NMR (DMSO, 101 MHz): δ 192.6, 187.5, 160.4, 144.1 (q, J=2.3 Hz), 140.6, 138.3, 135.3, 131.9, 125.8, 122.7, 121.5, 121.0 (q, J=255.6 Hz, $CF_3$), 117.2, 114.1, 113.7, 112.9, 111.7, 56.8.

Compound (S)-2-(4-chloro-2-methoxyphenyl)-2-((3-methoxy-5-(methylsulfonyl)phenyl)-amino)-1-(5-(trifluoromethoxy)-1H-indol-3-yl)ethenone (D) was prepared following steps 3 and 4 as disclosed in Example 1.

Example 7. Synthesis of a Compound of Formula (I): (S)-2-(4-chloro-2-methoxyphenyl)-2-((3-methoxy-5-(methylsulfonyl)phenyl)amino)-1-(5-(trifluoromethoxy)-1H-indol-3-yl)ethenone

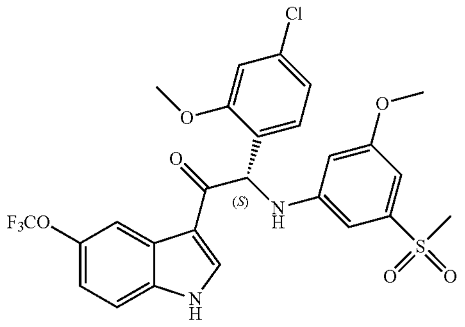

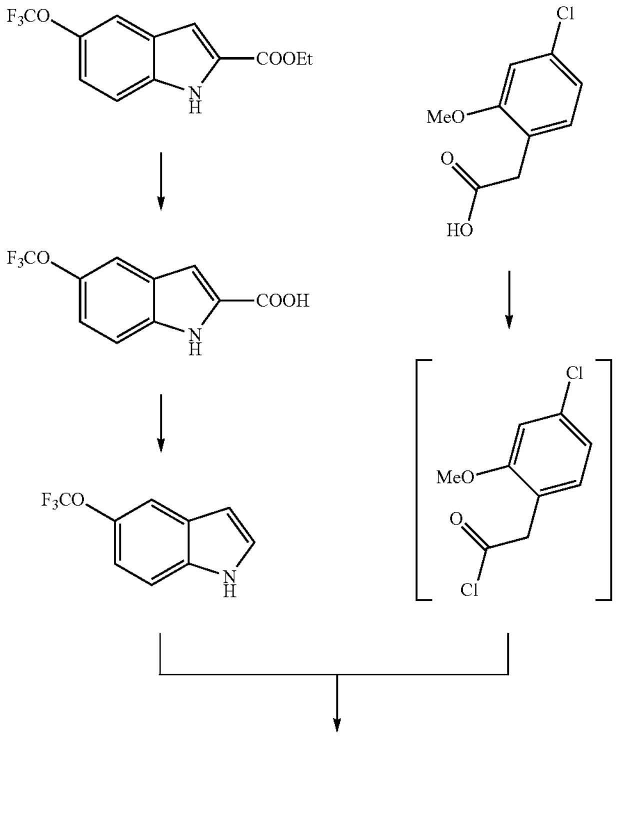

-continued
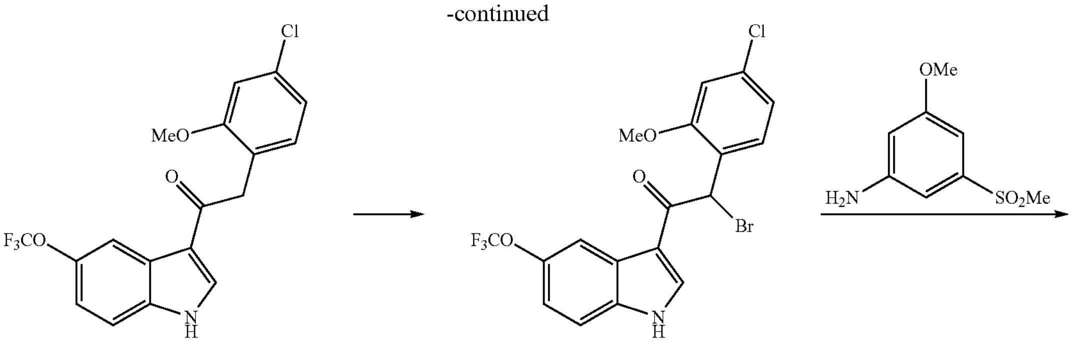
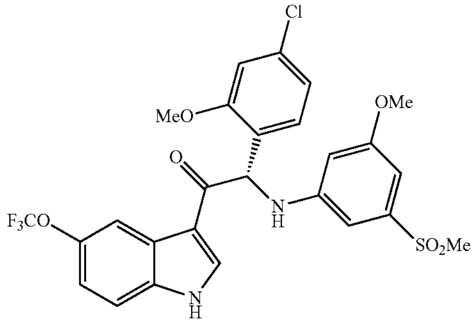
and
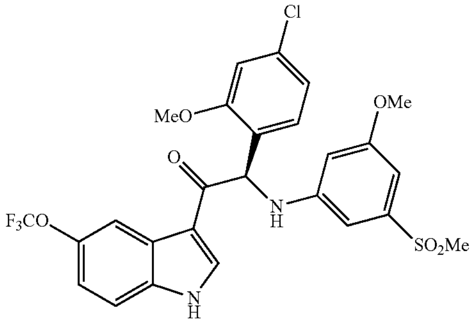
(1:1)
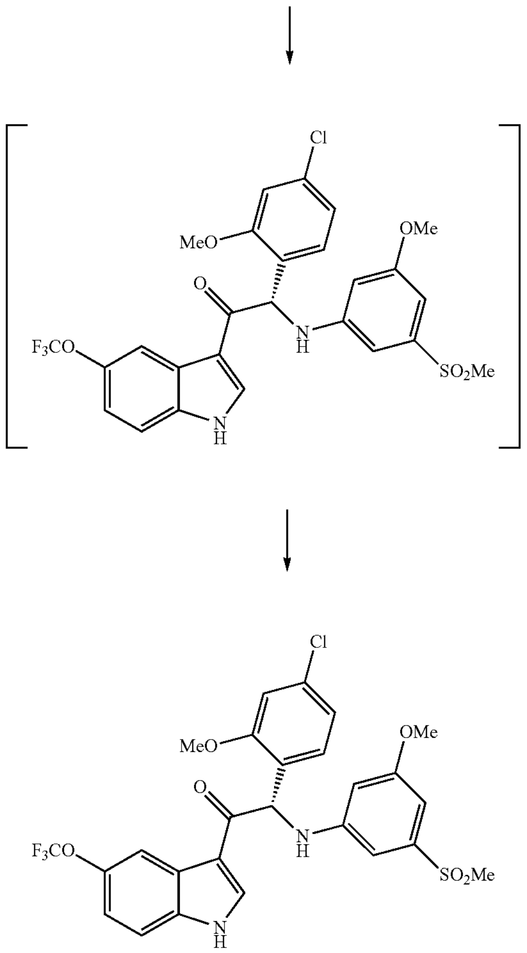

Step 1. Synthesis of 5-(trifluoromethoxy)-1H-indole-2-carboxylic Acid

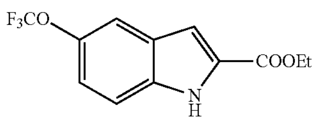 [SMILES: CCOC(=O)c1cc2cc(OC(F)(F)F)ccc2[nH]1]

Ethyl 5-(trifluoromethoxy)-1H-indole-2-carboxylate was dissolved in a mixture of water and methanol, and hydrolysed in the presence of sodium hydroxide to afford the product.

Step 2. Synthesis of 5-(trifluoromethoxy)-1H-indole

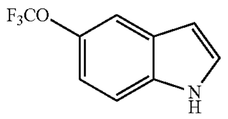 [SMILES: FC(F)(F)Oc1ccc2[nH]ccc2c1]

5-(trifluoromethoxy)-1H-indole-2-carboxylic acid was decarboxylated with copper and quinoline to afford the title compound.

Step 3. Synthesis of 2-(4-chloro-2-methoxyphenyl)-1-(5-(trifluoromethoxy)-1H-indol-3-yl)ethenone

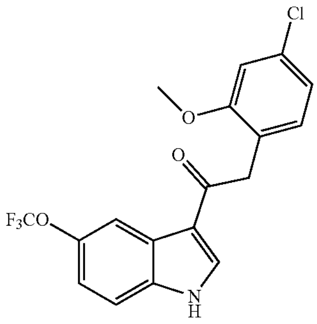 [SMILES: COc1cc(Cl)ccc1CC(=O)c1c[nH]c2ccc(OC(F)(F)F)cc12]

This compound was obtained as described in Step 1 of Example 1.

Step 4. Synthesis of 2-bromo-2-(4-chloro-2-methoxyphenyl)-1-(5-(trifluoromethoxy)-1H-indol-3-yl)ethanone

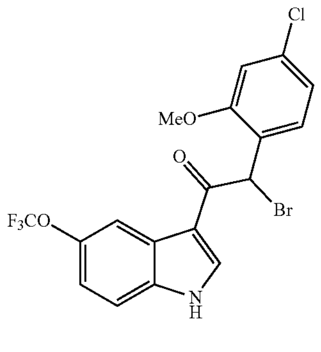 [SMILES: COc1cc(Cl)ccc1C(Br)C(=O)c1c[nH]c2ccc(OC(F)(F)F)cc12]

2-(4-chloro-2-methoxyphenyl)-1-(5-(trifluoromethoxy)-1H-indol-3-yl)ethanone was brominated with phenyltrimethylammonium tribromide in tetrahydrofuran. After completion of the reaction, the mixture was partially concentrated and aqueous sodium sulfite was added. The precipitate was isolated, washed with water and dried.

Step 5. Synthesis of 2-(4-chloro-2-methoxyphenyl)-2-[[3-methoxy-5-(methylsulfonyl)-phenyl]amino]-1-[5-(trifluoromethoxy)-1H-indol-3-yl]ethanone

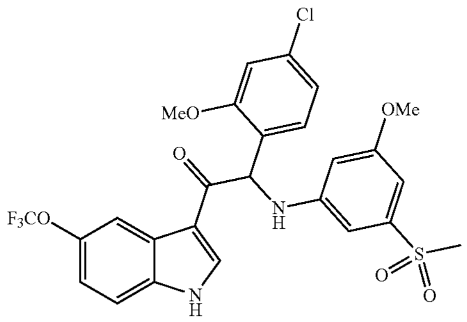 [SMILES: COc1cc(NC(C(=O)c2c[nH]c3ccc(OC(F)(F)F)cc23)c2ccc(Cl)cc2OC)cc(S(C)(=O)=O)c1]

2-bromo-2-(4-chloro-2-methoxyphenyl)-1-(5-(trifluoromethoxy)-1H-indol-3-yl)ethanone was coupled with 3-methoxy-5-(methylsulfonyl)aniline in a mixture of toluene and an aqueous buffer solution of sodium dihydrogen phosphate dihydrate and dipotassium hydrogen phosphate trihydrate, using tetrabutylammonium bromide (TBAB) as a phase transfer catalyst. After completion of the reaction, the reaction mixture was treated with 2-methyl-tetrahydrofuran (2-MeTHF). After removal of the aqueous layer, the organic layer was partially concentrated and more 2-MeTHF was added, followed by dilute hydrochloric acid washes and aqueous sodium sulfate washes. The organic layer was then partially concentrated and treated with n-heptane. The crystallized product was isolated, washed with water and with n-heptane, and dried.

Step 6. Obtention of (2S)-2-(4-chloro-2-methoxyphenyl)-2-[[3-methoxy-5-(methyl-sulfonyl)phenyl]amino]-1-[5-(trifluoromethoxy)-1H-indol-3-yl]ethenone 2-(4-chloro-2-methoxyphenyl)-2-[[3-methoxy-5-(methylsulfonyl)phenyl] amino]-1-[5-(trifluoromethoxy)-1H-indol-3-yl]ethanone was dissolved in a mixture of acetonitrile and methanol and purified by chiral chromatography (eluent: acetonitrile/methanol). Subsequently, a solvent switch to methanol was performed and the resulting solution containing the title compound was partially concentrated and water was added. The crystallized product was isolated, washed with methanol/water and dried.

The invention claimed is:

1. A process for the preparation of a compound of formula (I)

(I)

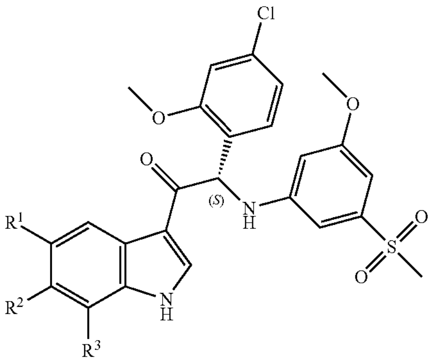

comprising the steps of:

a) reacting a compound of formula (II) with 3-methoxy-5-methylsulfonyl-aniline to produce a compound of formula (III); and (II)

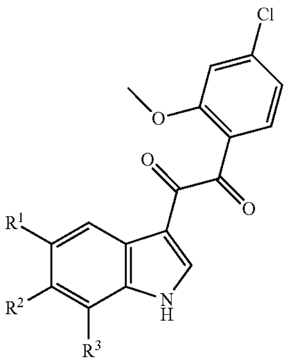

(III)

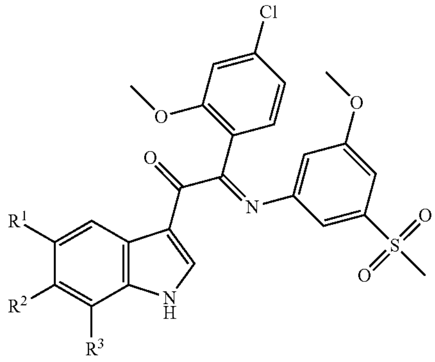

b) hydrogenation of the compound of formula (III) to produce the compound of formula (I);

wherein:

$R^1$ is H, $R^2$ is F and $R^3$ is H or $CH_3$;

$R^1$ is H, $CH_3$ or F, $R^2$ is $OCH_3$ and $R^3$ is H;

$R^1$ is H, $R^2$ is $OCH_3$ and $R^3$ is $CH_3$;

$R^1$ is $CH_3$, $R^2$ is F and $R^3$ is H;

$R^1$ is $CF_3$ or $OCF_3$, $R^2$ is H and $R^3$ is H;

$R^1$ is $OCF_3$, $R^2$ is $OCH_3$ and $R^3$ is H; or $R^1$ is $OCF_3$, $R^2$ is H and $R^3$ is $CH_3$.

2. The process according to claim 1, wherein the compound of formula (II) is prepared by a method comprising the steps of:

i) converting 2-(4-chloro-2-methoxy-phenyl) acetic acid (IX) into a compound of formula (Xa), wherein X is Cl or Br;

(IX)

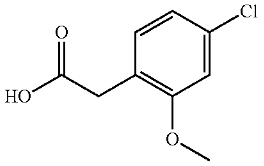

(Xa)

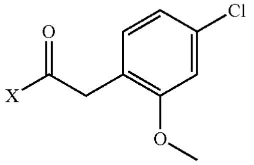

ii) reacting the compound of formula (Xa) with a compound of formula (XI) to produce a compound of formula (XII);

(XI)

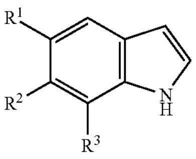

(XII)

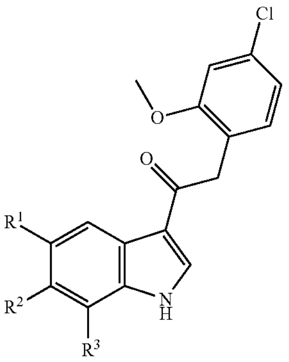

iii) contacting the compound of formula (XII) with an oxidizing agent to produce the compound of formula (II);

wherein $R^1$, $R^2$ and $R^3$ are as defined in claim 1.

3. The process according to claim 1, wherein the compound of formula (II) is prepared by a method comprising the steps of:

i) reacting a compound of formula (XI) with oxalyl chloride to produce a compound of formula (XIII);

(XI)

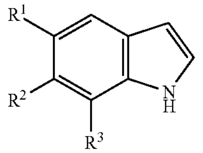

(XIII)

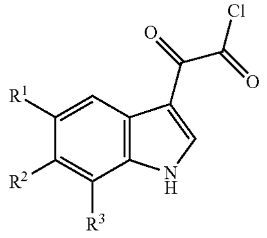

ii) contacting the compound of formula (XIII) with a compound selected from the group consisting of: (4-chloro-2-methoxyphenyl) magnesium bromide, (4-chloro-2-methoxyphenyl) magnesium chloride, (4-chloro-2-methoxyphenyl) magnesium iodide, (4-chloro-2-methoxyphenyl) Zinc bromide, (4-chloro-2-methoxyphenyl) Zinc chloride and (4-chloro-2-methoxyphenyl) Zinc iodide, to afford a compound of formula (II);

wherein $R^1$, $R^2$ and $R^3$ are as defined in claim 1.

4. The process according to claim 1, wherein the compound of formula (II) is prepared by a method comprising the steps of:

i) reacting a compound of formula (XI) with oxalyl chloride to produce a compound of formula (XIII);

(XI)

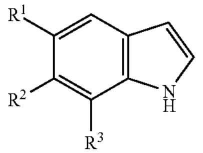

(XIII)

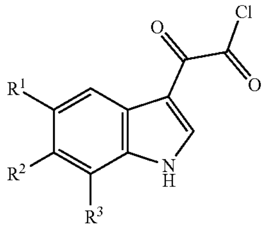

ii) reacting the compound of formula (XIII) with 3-chlorophenol to produce a compound of formula (XVI);

(XVI)

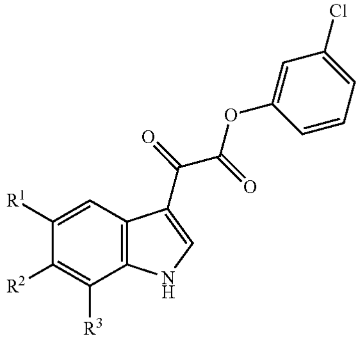

iii) submitting the compound of formula (XVI) to acidic conditions to afford a compound of formula (XVII);

(XVII)

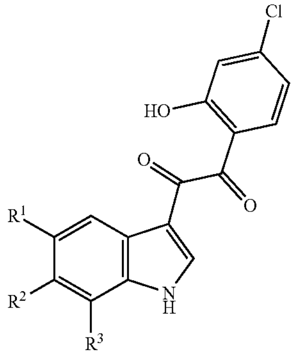

iv) methylation of the compound of formula (XVII) to afford the compound of formula (II);

wherein $R^1$, $R^2$ and $R^3$ are as defined in claim 1.

5. The process according to claim 1, wherein the compound of formula (II) is prepared by a method comprising the steps of:

i) reacting 4-chloro-2-methoxybenzaldehyde with a compound of formula (XVIII) to afford a compound of formula (XIX), wherein PG is a protecting group selected from the group consisting of benzyl, methyl, acetyl, and tosyl;

and (XVIII)

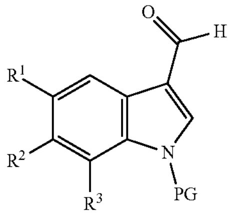

-continued (XIX)

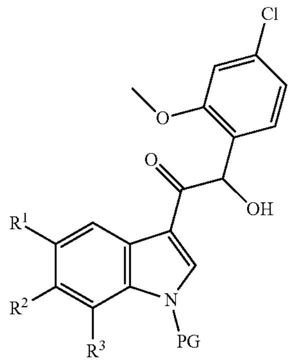

ii) contacting the compound of formula (XIX) with an oxidizing agent to produce the compound of formula (II);

wherein $R^1$, $R^2$ and $R^3$ are as defined in claim 1.

6. The process according to claim 1, wherein the compound of formula (II) is prepared by a method comprising the steps of:

i) reacting 1-(4-chloro-2-methoxy-phenyl)-2,2-dihydroxy-ethanone with a compound of formula (XI) to afford a compound of formula (XX);

(XI)

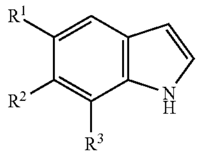

(XX)

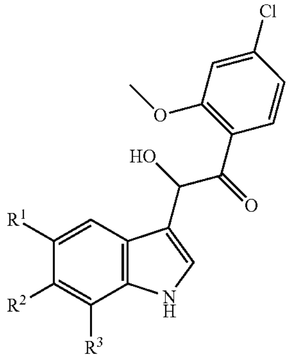

ii) reacting the compound of formula (XX) with an oxidizing agent to afford the compound of formula (II);

wherein $R^1$, $R^2$ and $R^3$ are as defined in claim 1.

7. The process according to claim 1, wherein the compound of formula (II) is prepared by a method comprising the steps of:

i) reacting a compound of formula (XXV) with a base selected from the group consisting of LiOtBu, LiHMDS, LiOEt, LiOMe and LiOH to produce a compound of formula (XXVI);

(XXV)

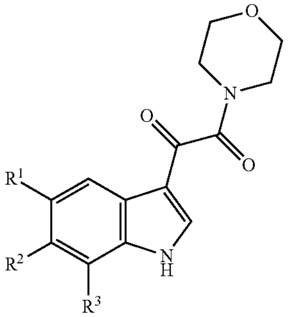

(XXVI)

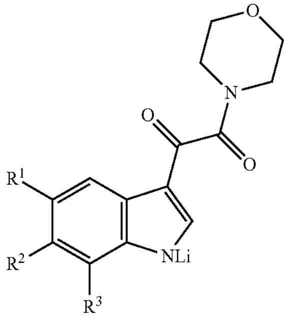

ii) reacting the compound of formula (XXVI) with 4-chloro-2-methoxyphenyl magnesium halide or with (4-chloro-2-methoxyphenyl) Lithium to produce the compound of formula (II);

wherein $R^1$, $R^2$ and $R^3$ are as defined in claim 1.

8. The process according to claim 1, wherein the step of reacting a compound of formula (II) with 3-methoxy-5-methylsulfonyl-aniline to produce a compound of formula (III) is performed in the presence of at least one reagent selected from the group consisting of p-TsOH, MSA, TFA, dichloroacetic acid (DCA), saccharin, $Ca(OTf)_2$, $ZnBr_2$, $Zn(OTf)_2$, $TiCl_4$, Ti $(i-PrO)_4$, Ti $(EtO)_4$, $FeCl_3$, CuBr, $ZnCl_2$, TfOH and $Ba(OTf)_2$.

9. The process according to claim 1, wherein the step of hydrogenating the compound of formula (III) to produce a compound of formula (I) is performed in the presence of a combination of bis(norbornadiene) rhodium (I) tetrafluoroborate and(S)-1-[(RP)-2-(diphenylphosphino)ferrocenyl] ethyldi-tert-butylphosphine.

10. The process according to claim 1, wherein the step of hydrogenating the compound of formula (III) to produce a compound of formula (I) is performed in the presence of a combination of the ruthenium catalyst Ru(COD) (TFA) 2 and the ligand(S)-DM-SEGPHOS.

11. A process for the preparation of a compound of formula (I)

(I)

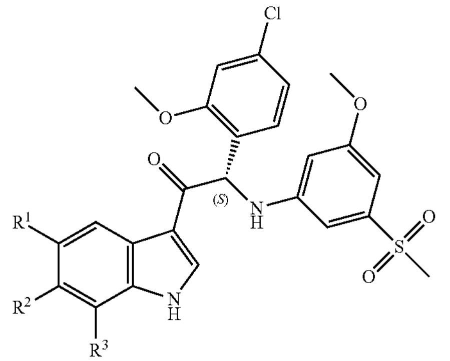

comprising the steps of:

1) Reacting a compound of formula (XXVII) with 3-methoxy-5-methylsulfonyl-aniline in the presence of a suitable phase transfer catalyst to produce a compound of formula (XXVIII);

(XXVII)

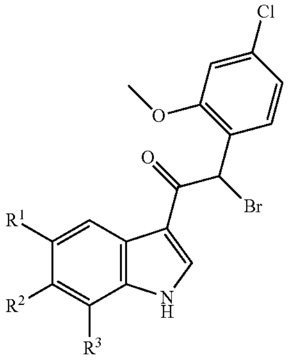

(XXVIII)

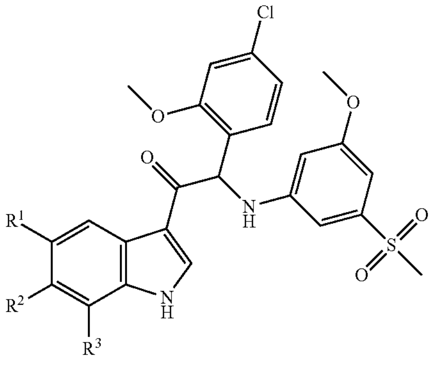

2) Chiral separation of the compound of formula (XXVIII) to produce the compound of formula (I);

wherein:

$R^1$ is H, $R^2$ is F and $R^3$ is H or $CH_3$;
$R^1$ is H, $CH_3$ or F, $R^2$ is $OCH_3$ and $R^3$ is H;
$R^1$ is H, $R^2$ is $OCH_3$ and $R^3$ is $CH_3$;
$R^1$ is $CH_3$, $R^2$ is F and $R^3$ is H;
$R^1$ is $CF_3$ or $OCF_3$, $R^2$ is H and $R^3$ is H;
$R^1$ is $OCF_3$, $R^2$ is $OCH_3$ and $R^3$ is H; or
$R^1$ is $OCF_3$, $R^2$ is H and $R^3$ is $CH_3$.

12. The process according to claim 11, wherein the reaction is performed using tetrabutylammonium bromide and a buffer solution of sodium dihydrogen phosphate dihydrate and dipotassium hydrogen phosphate trihydrate.

13. The process according to claim 1, wherein $R^1$ is $OCF_3$, $R^2$ is H and $R^3$ is H.

14. A process for the preparation of a compound of formula (I)

(I)

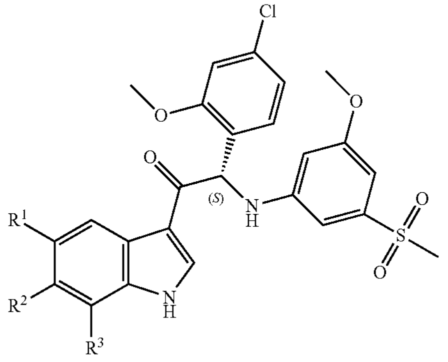

wherein $R^1$ is H, $R^2$ is F and $R^3$ is H or $CH_3$;
$R^1$ is H, $CH_3$ or F, $R^2$ is $OCH_3$ and $R^3$ is H;
$R^1$ is H, $R^2$ is $OCH_3$ and $R^3$ is $CH_3$;
$R^1$ is $CH_3$, $R^2$ is F and $R^3$ is H;
$R^1$ is $CF_3$ or $OCF_3$, $R^2$ is H and $R^3$ is H;
$R^1$ is $OCF_3$, $R^2$ is $OCH_3$ and $R^3$ is H; or
$R^1$ is $OCF_3$, $R^2$ is H and $R^3$ is $CH_3$;
characterized by hydrogenation of compound of formula (III)

(III)

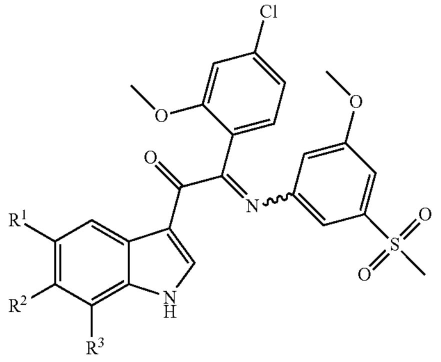

wherein the hydrogenation is performed in the presence of a combination of a catalyst and a chiral ligand.

15. The process according to claim 14, wherein the catalyst is bis(norbornadiene)-rhodium (I) tetrafluoroborate and the chiral ligand is(S)-1-[(RP)-2-(diphenylphosphino) ferrocenyl]ethyldi-tert-butylphosphine.

16. The process according to claim 11, wherein $R^1$ is $OCF_3$, $R^2$ is H and $R^3$ is H.

17. The process according to claim 14, wherein $R^1$ is $OCF_3$, $R^2$ is H and $R^3$ is H.

18. The process according to claim 7, wherein the halide is Br, Cl or I.

* * * * *